United States Patent [19]

Kozuka et al.

[11] 3,980,622
[45] Sept. 14, 1976

[54] POLYMERIZABLE EMULSIFYING AGENT AND APPLICATION THEREOF

[75] Inventors: Ko Kozuka, Takasago; Shigeru Kobayashi, Akashi; Akira Watanabe, Kobe; Yoshio Iki, Akashi; Masaaki Yokoe, Takasago, all of Japan

[73] Assignee: Kanegafuchi Kagaku Kogyo Kabushiki Kaisha, Osaka, Japan

[22] Filed: May 23, 1975

[21] Appl. No.: 580,422

Related U.S. Application Data

[62] Division of Ser. No. 399,128, Sept. 20, 1973, Pat. No. 3,907,870.

[30] Foreign Application Priority Data

Sept. 20, 1972 Japan............................ 47-94797

[52] U.S. Cl. ............... 260/79.3 M; 260/29.6 AN; 260/29.6 T; 260/29.6 SQ; 526/240; 526/258; 526/323
[51] Int. Cl.² ................ C08F 28/02; C08G 75/20
[58] Field of Search ............ 260/29.6 AN, 29.6 SQ, 260/79.3 R, 79.3 M, 78.5 B, 78.5 E, 78.5 CL, 78.5 HC, 29.6 T; 526/258, 240, 323

[56] References Cited
UNITED STATES PATENTS

| | | | |
|---|---|---|---|
| 2,964,557 | 12/1960 | Niederhauser et al. | 260/486 R |
| 3,147,301 | 9/1964 | Sheetz | 260/485 J |
| 3,304,315 | 2/1967 | Nevin et al. | 260/485 R |
| 3,343,964 | 9/1967 | Thomas | 260/485 R |
| 3,391,183 | 7/1968 | Dowbenko | 260/485 R |
| 3,551,479 | 12/1970 | Emmons | 260/485 J |
| 3,579,565 | 5/1971 | Zaslowsky et al. | 260/485 J |
| 3,592,655 | 7/1971 | Dykstra | 260/79.3 MU |
| 3,660,527 | 5/1972 | Sakai et al. | 260/79.3 MU |
| 3,679,737 | 7/1972 | Pohleman et al. | 260/485 J |
| 3,830,830 | 8/1974 | Cleveland et al. | 260/485 R |
| 3,844,986 | 10/1974 | Tomatu et al. | 260/79.3 M |

FOREIGN PATENTS OR APPLICATIONS

1,161,668 8/1969 United Kingdom............ 260/485 J

*Primary Examiner*—Ronald W. Griffin
*Attorney, Agent, or Firm*—Armstrong, Nikaido & Wegner

[57] ABSTRACT

Compounds having the formula

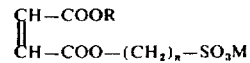

wherein R is alkyl group having 6 to 22 carbon atoms, M is H, Li, Na, K or $NH_4$ and n is an integer of 2 to 4, inclusive. The compound is useful as polymerizable emulsifying agent, and enables to improve properties of produced polymer and to provide a modacrylic fiber superior in heat stability and fastness to light. The aqueous emulsion polymerization of $\alpha,\beta$-ethylenically unsaturated monomer by the use of the polymerizable anionic emulsifying agent is capable of preventing a discharge of an environmental pollutant.

9 Claims, 9 Drawing Figures

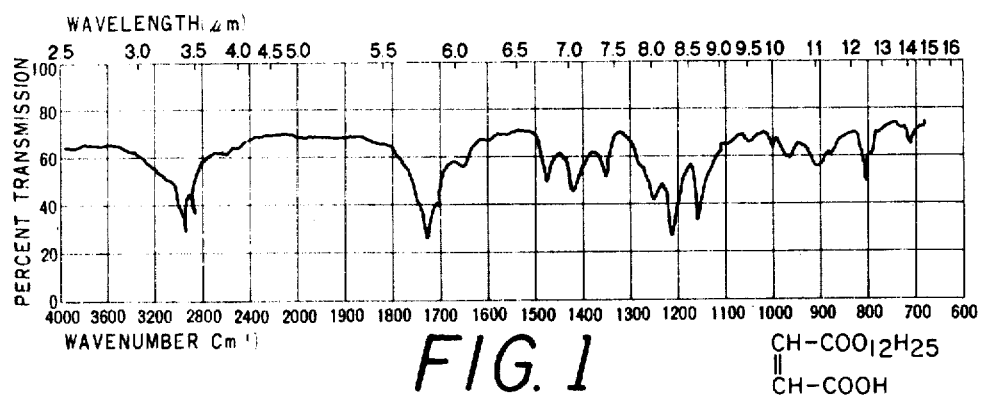
FIG. 1
$$\begin{array}{l}CH-COOC_{12}H_{25}\\ \parallel\\ CH-COOH\end{array}$$
FIG. 2
$$\begin{array}{l}CH-COOC_{12}H_{25}\\ \parallel\\ CH-COONa\end{array}$$
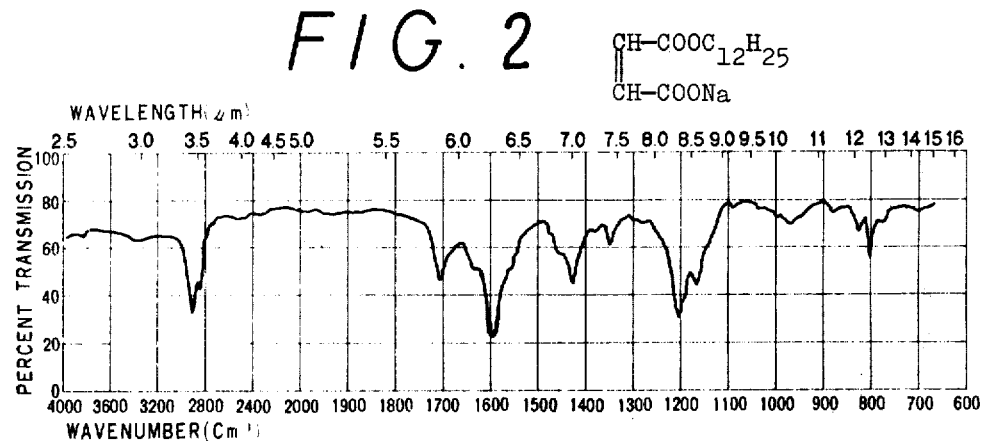
FIG. 3
$$\begin{array}{l}CH-COOC_{12}H_{25}\\ \parallel\\ CH-COO-(CH_2)_3-SO_3Na\end{array}$$
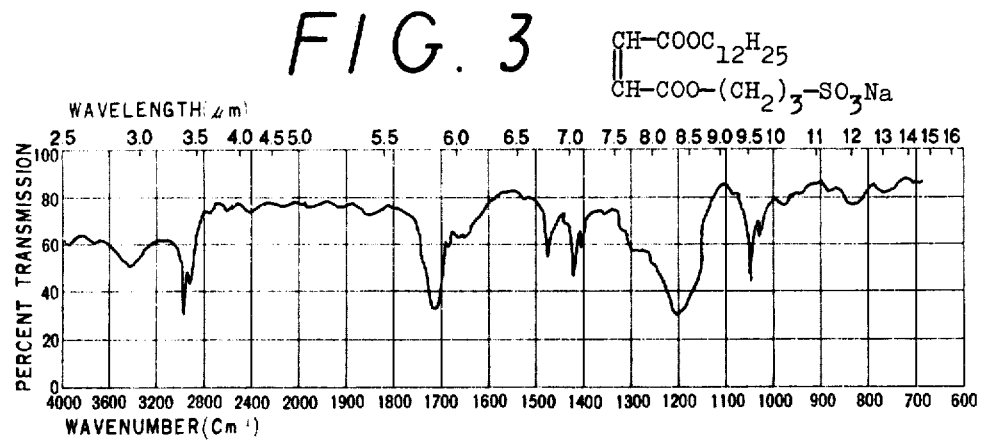

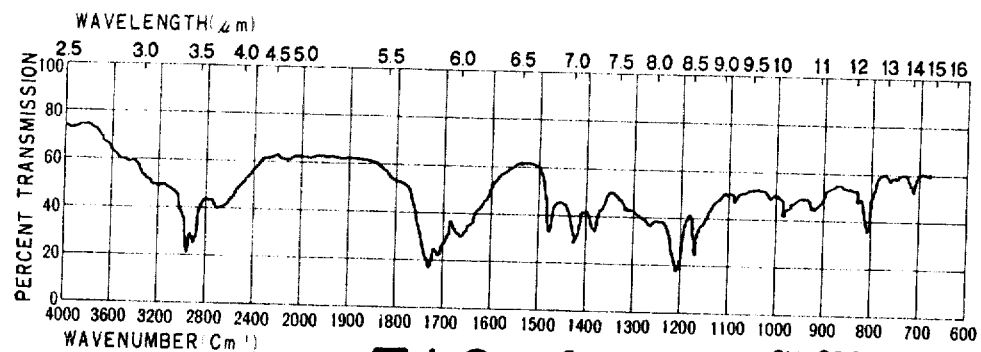
FIG. 4
FIG. 5
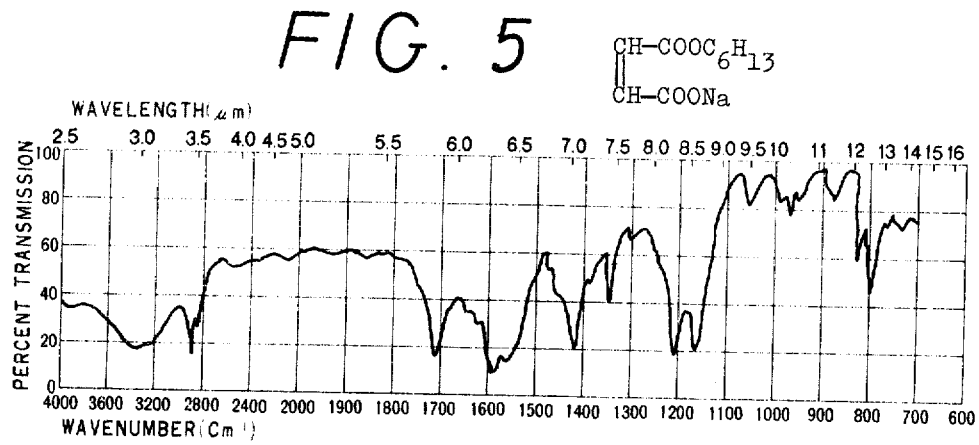
FIG. 6
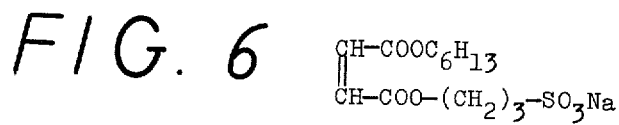
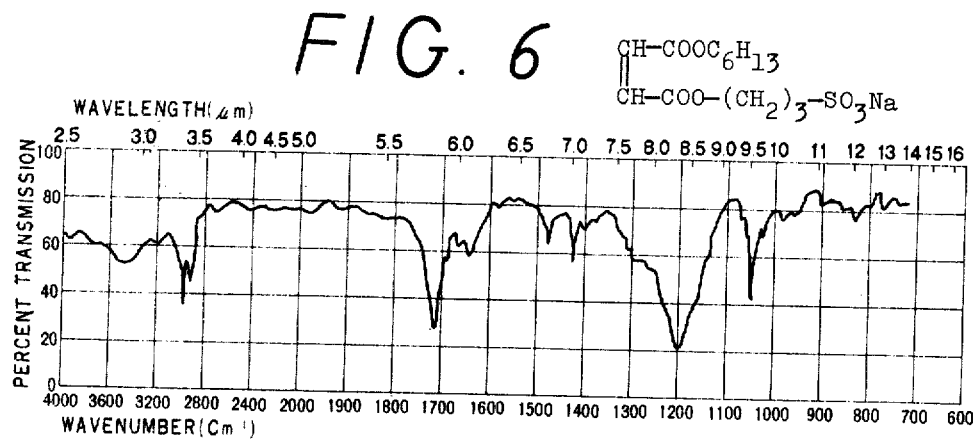

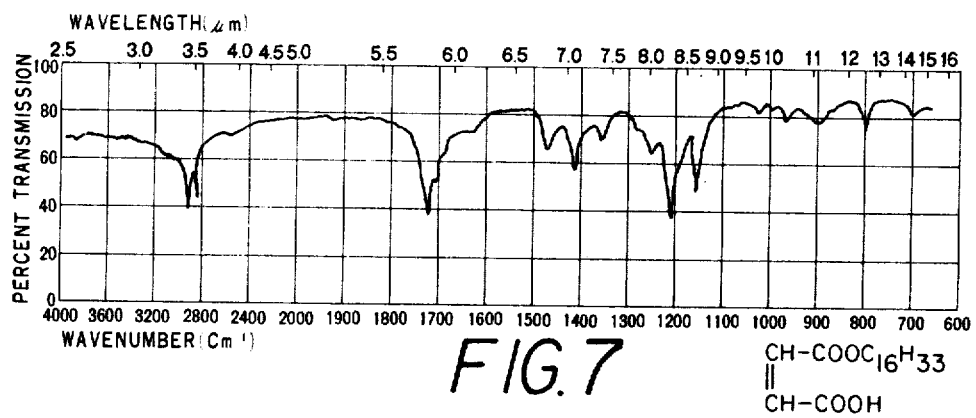
FIG. 7  CH-COOC$_{16}$H$_{33}$ ‖ CH-COOH
FIG. 8  CH-COOC$_{16}$H$_{33}$ ‖ CH-COONa
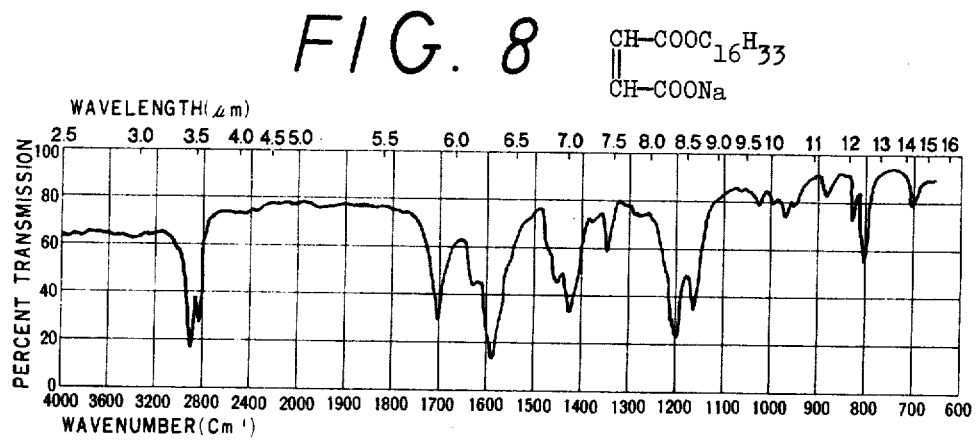
FIG. 9  CH-COOC$_{16}$H$_{33}$ ‖ CH-COO-(CH$_2$)$_3$-SO$_3$Na
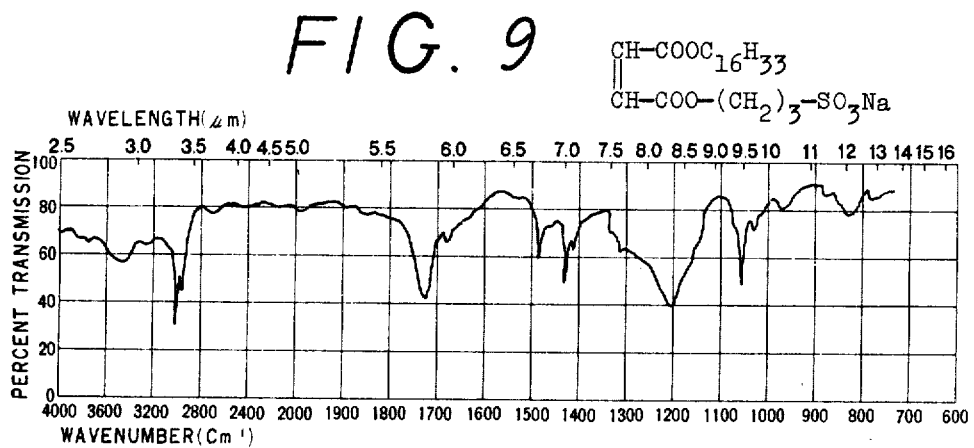

POLYMERIZABLE EMULSIFYING AGENT AND APPLICATION THEREOF

This is a division of application Ser. No. 399,128 filed Sept. 20, 1973, now U.S. Pat. No. 3,907,870.

BACKGROUND OF THE INVENTION

The present invention relates to a novel polymerizable emulsifying agent, and more particularly relates to a novel polymerizable emulsifying agent providing an aqueous emulsion polymerization process for $\alpha,\beta$-ethylenically unsaturated monomer which does not discharge an environmental pollutant such as emulsifying agent, water-soluble polymeric material, water-soluble oligomer or oil-soluble oligomer in such a step as filtration or washing of polymer by polymerizing the polymerizable emulsifying agent and the specific $\alpha,\beta$-ethylenically unsaturated monomer polymerizable therewith.

The present invention further relates to a novel polymerizable emulsifying agent which is polymerized with acrylonitrile to provide a modacrylic fiber superior in heat stability and fastness to light.

The polymerizable emulsifying agent of the present invention is sulfoalkyl-alkylmaleates having one hydrophobic alkyl group and one hydrophilic sulfoalkyl group which is prepared from maleic anhydride, higher alcohol and one of propanesultone, butanesultone, sodium 2-oxy-ethanesulfonate and sodium isethionate. The polymerizable emulsifying agent of the invention is effectively employed in a polymerization of $\alpha,\beta$-ethylenically unsaturated monomer so as to prevent discharge of environmental pollutants by industrial wastes, also effectively employed for improving properties such as heat stability, mechanical property, transparency and processing property of synthetic resins such as copolymer of acrylonitrile and others.

An aqueous emulsion polymerization process has been utilized to prepare a polymerized material in a field such as synthetic rubber, synthetic resin, coating material or synthetic fiber. In such a process, after polymerization, the polymerized material is taken out as an intermediate product or a product through steps such as filtration from an aqueous medium, washing and drying, and frequently environmental pollutants such as water-soluble polymeric material, water-soluble or oil-soluble oligomer, which are by-produced in polymerization, as well as emulsifying agent are discharged into drainage at the time of filtration or washing of a polymerized material. In recent years, the recognition concerning toxicity of emulsifying agent becomes deepened, and also a water-soluble polymeric material and a water-soluble or oil-soluble oligomer may pollute water since they are pollutants being capable of giving chemical oxygen demand (COD) load and biological oxygen demand (BOD) load which exhaust a large amount of oxygen dissolved in water when they are decomposed by microorganisms. A water pollution such as sea water area, rivers, lakes and marshes or public water area has recently constituted a serious social problem as one of an environmental pollutants, and a countermeasure against a polymerization drainage as stated above has been strongly desired.

Hitherto, an aqueous emulsion polymerization process has been utilized in preparation of various polymers with industrial advantages that it produces less scale or coagula in comparison with another aqueous polymerization process, reaction heat in polymerization is readily removed and polymerization reaction can be stably carried out even at high monomer concentration.

However, a conventional emulsifying agent is not polymerizable and it is merely adsorbed on a surface of polymer particle. Then various unfavorable things arise since it does not bond chemically to a polymer. For instance, in case of processing a polymer to shaped article such as film, fiber, or the like, an emulsifying agent must be removed off completely from polymer since an emulsifying agent remaining in polymer makes the properties such as transparency, heat stability, mechanical property, fastness to light and water resistance worse. For the removal of an emulsifying agent, a large amount of wash water must be employed, which is still insufficient.

On the other hand, there has been known a polymerizable aninonic emulsifying agent, for instance, sulfo ester of $\alpha$-methylene carboxylic acid derivatives such as sodium 2-sulfoethyl-$\alpha$-methylacrylate, sodium 2-sulfoethyl-$\alpha$-butylacrylate and sodium 2-sulfoethyl-$\alpha$-hexylacrylate, monoalkylitaconoxypropanesulfonate derivatives such as potassium monolaurylitaconoxypropanesulfonate and sodium monocetyilitaconoxypropanesulfonate, sodium p-styrelundecanoate, sodium 10-acrylamidestearate or sodium 10-acryloxystearate. These polymerizable emulsifying agents contribute to improve the mechanical stability and the pigment dispersion of latex, or the wet strength, the water resistance and the adhesiveness of film or coated material. However, in case of recovering a polymer from latex prepared by employing the above-mentioned emulsifying agent through passing the salting-out, filtration, washing and drying to give the desired polymer, the employment of such an emulsifying agent reveals the following defects at the time of polymerization. For instance, in case of polymerizing $\alpha,\beta$-ethylenically unsaturated monomer by employing a sulfo ester of $\alpha$-methylene carboxylic acid derivatives or monoalkylitaconoxypropanesulfonate derivatives as a polymerizable emulsifying agent, a homopolymer of the polymerizable emulsifying agent, or a water-soluble copolymer or a liquid oligomer which is abundant in the polymerizable emulsifying agent is apt to be by-produced since such a polymerizable emulsifying agent is readily homopolymerized or copolymerized. In case of polymerizing an $\alpha,\beta$-ethylenically unsaturated monomer by employing a polymerizable emulsifying agent such as sodium 10-acrylamidestearate or sodium 10-acryloxystearate, a homopolymer of the polymerizable emulsifying agent is apt to be by-produced or the unreacted polymerizable emulsifying agent is apt to remain comparatively in large quantities since such a polymerizable emulsifying agent is readily homopolymerized but hardly copolymerized. These by-products and the residue are abundantly discharged together with a drainage because they are difficult to recover. Therefore, such conventional polymerizable emulsifying agents also have the disadvantage in the point of environmental pollution though they are effective in improving properties as mentioned above.

Furthermore, there has been known as acrylonitrile copolymer for modacrylic fiber, especially the copolymer containing 30 to 80 % by weight of acrylonitrile, which is prepared by an aqueous emulsion polymerization process employing a usual emulsifying agent. However, such a copolymer contains a small amount of emulsifying agent even though water wash is completed as much as possible on industrial scale, and a modacrylic fiber prepared therefrom is inferior in heat stability and fastness to light due to the residual emulsifying agent. Therefore, commercial value of modacrylic fiber has been discounted in spite of its excellent properties such as flame resistance, high bulkiness, lusterness and hand touchness. For the purpose of decreasing the residual amount of emulsifying agent in the copolymer, the present inventors have carried out an emulsion polymerization by employing the aforementioned known polymerizable emulsifying agent. However, it has been found out that heat stability and fastness to light are not improved though the employed polymerizable emulsifying agent is copolymerized with acrylonitrile to be bonded chemically within the polymer molecule. Besides, under certain circumstances, softening temperature of the copolymer was lowered as a result of introducing a substituent group which is bulky in excess as a side-chain of the copolymer by means of copolymerizing an polymerizable emulsifying agent. As such examples, monoalkylitaconoxypropanesulfonate derivatives such as sodium monolaurylitaconoxypropanesulfonate are mentioned.

OBJECT OF THE INVENTION

It is an object of the present invention to provide a novel polymerizable emulsifying agent.

Another object of the invention is to provide a novel polymerizable emulsifying agent capable of preventing a discharge of an environmental pollutant such as emulsifying agent, water-soluble polymeric material, water-soluble oligomer or oil-soluble oligomer in an aqueous emulsion polymerization of $\alpha,\beta$-ethylenically unsaturated monomer.

Further object of the invention is to provide a novel polymerizable emulsifying agent which can give a polymer improved in properties such as transparency, heat stability, mechanical property, fastness to light, impact strength, heat flowability and processing property.

More further object of the invention is to provide a novel process for emulsion-polymerizing $\alpha,\beta$-ethylenically unsaturated monomer employing the specific polymerizable emulsifying agent.

Still further object of the invention is to provide an improved aqueous emulsion polymerization process for $\alpha,\beta$-ethylenically unsaturated monomer which does not discharge an environmental pollutant such as emulsifying agent, water-soluble polymeric material, water-soluble oligomer or oil-soluble oligomer in a step such as filtration and washing of polymer.

Still more further object of the invention is to provide a modacrylic fiber superior in heat stability and fastness to light.

These and other objects of the invention will become apparent from the description hereinafter.

DESCRIPTION OF THE INVENTION

It has now been found that the above-mentioned objects are accomplished by a new polymerizable anionic emulsifying agent having the following general formula:

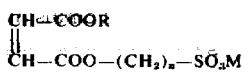

wherein R is alkyl group having 6 to 22 carbons atoms, M is H, Li, Na, K or $NH_4$ and $n$ is an integer of 2 to 4, inclusive.

FIGS. 1 to 9 are infrared spectrums of the first intermediate, the second intermediate and the polymerizable anionic emulsifying agent of the present invention.

The polymerizable anionic emulsifying agents of the present invention, sulfonalkyl-alkylmaleates, are prepared as follows:

The first intermediary monoalkylmaleate is prepared by reacting maleic anhydride and higher alcohol, and hydroxide of alkali metal or ammonium is reacted therewith to give the secondary intermediary alkali metal salt or ammonium salt of monoalkylmaleate. Then, by reacting the second intermediate and a sulfonating agent such as propanesultone, butanesultone or sodium 2-oxy-ethanesulfonate, end product of alkali salt or ammonium salt of sulfoalkyl-alkylmaleate is prepared.

The first intermediary monoalkylmaleate is prepared in high yield of 90 to 95 % by reacting equimolar amounts of maleic anhydride and higher alcohol at a reaction temperature of 50° to 100°C., preferably 60° to 80°C. for 2 to 3 hours in the absence of solvent. As a starting material, maleic anhydride is advantageously employed more than maleic acid by the following reason. In case of employing maleic acid, dialkylmaleate is apt to be by-produced since the reaction must be proceeded at higher temperature in the presence of dehydrating agent such as mineral acid or aromatic sulfonic acid. In case of employing maleic anhydride, monoalkylmaleate is readily and quantitatively prepared at a moderate reaction temperature in the absence of dehydrating agent. Also as a higher alcohol, straightchain alcohol, branched alcohol, primaly alcohol, secondary alcohol and tertiary alcohol are employed irrespective of carbon number within the range of 6 to 22 carbon atoms. Further phenyl ethers such as phenyl ether of polyethylene glycol or phenyl ethers of polypropylene glycol may be employed as a starting material for the polymerizable anionic emulsifying agent. Also, a mixture of higher alcohols having carbon atoms substantially distributing in the range of 9 to 15 may be employed.

The secondary intermediary alkali metal salt or ammonium salt of monoalkylmaleate is prepared by adding powdery alkali metal hydroxide or a concentrated aqueous solution of alkali metal hydroxide, preferably 30 to 50 % by weight aqueous solution, or an aqueous ammonia, preferably 30 to 50 % by weight aqueous ammonia into monoalkylmaleate dissolved in organic solvent such as acetone, methanol or isopropanol, at a temperature of 20° to 60°C. The hydroxide of alkali metal or ammonium is employed in an amount equimolar with monoalkylmaleate. In the above neutralizing reaction, the dispersibility of alkali is improved by employing the organic solvent as a reaction medium, and also the viscosity of the obtained dispersions of alkali metal salt or ammonium salt of monoalkylmaleate is lowered by employing the organic solvent. The organic solvent is preferably employed in an amount more than the amount of the employed alkali. In case of employing the organic solvent in such amount, there is no limitation to proceed the reaction. However, it is preferable to employ the organic solvent in an amount less than 20 times the amount of the employed alkali in order to distil off the solvent economically after the conclusion of the reaction. In case of employing the organic solvent in less amount, the agitation becomes difficult since the viscosity of the reaction mixture increases. As an organic solvent, it is necessary to employ one which does not react with the added alkali, and also does not form an azeotropic mixture with water produced by the neutralizing reaction between monoalkylmaleate and alkali. As an organic solvent, it is also necessary to employ one which does not react with the sulfonating agent such as sultones or sodium 2-oxy-ethanesulfonate in the next step, and moreover is readily recovered in the final step. By such reasons, acetone or methanol is suitably employed. Though isopropanol may also be employed, it is somewhat troublesome to separate completely it from the end product. Further, it is possible to neutralize monoalkylmaleate with aqueous solution of alkali metal hydroxide or aqueous ammonia and then to proceed the next sulfonation reaction in the aqueous medium. However, the ester value of the end product is lower than the case of the reaction in the organic solvent such as acetone since the sulfonating agent such as sultones ring-opens to the extent of 5 to 8 % by weight. In case of employing the powdery alkali metal hydroxide, the neutralizing reaction is carried out by suspending the powder in the organic solvent having large polarity such as alcohol for fear that the ester bond is hydrolyzed during the neutralizing reaction of monoalkylmaleate. However, also in the aqueous alkaline solution or in the aqueous alkaline solution-organic solvent, the neutralizing reaction is proceeded in high yield, as shown in the following Table 1, by adjusting the reaction temperature below about 60°C. Especially, in case of employing the acetone-water reaction medium or the methanol-water reaction medium, the end product is readily taken out and the organic solvent is also readily recovered since the second intermediate and the end product are well dissolved in the above reaction medium to give a uniform solution.

TABLE 1

| Reaction temp. | Time required in adding 50 % NaOH aqueous solution | Monolauryl-maleate in 1 ml. acetone | Yield of sodium mono-laurylmaleate |
|---|---|---|---|
| °C. | min. | g. | % |
| 40 – 55 | 0.1 | 0.7 | 94 |
| 58 – 59 | 0.5 | 0.7 | 93 |
| 58 – 61 | 12.0 | 1.4 | 93 |
| 58 – 61 | 20.0 | 0.7 | 99 |

The end product, alkali metal salt or ammonium salt of sulfoalkyl-alkylmaleate, is prepared by reacting equimolar amounts of the second intermediate and the sulfonating agent such as propanesultone, butanesultone or sodium 2-oxy-ethanesulfonate, in the presence of the same organic solvent as employed in the preparation of the second intermediate at a temperature of 50° to 85°C. for 1 to 4 hours. The end product is also prepared by reacting the first intermediary monoalkylmaleate and sodium isethionate in the presence of acidic catalyst. As the sulfonating agent, propanesultone is employed effectively more than butanesultone since the sulfonation is completed for a short time of 1.5 to 2 hours under a moderate condition due to its large reactivity. In case of employing sodium 2-oxy-ethanesulfonate as a sulfonating agent, it is necessary to raise a reaction temperature and it is disadvantageous to employ them compared with sultones. The sulfonation by sodium 2-oxy-ethanesulfonate is completed for 8 to 10 hours at a moderate temperature of about 80°C. by employing hydrogen chloride gas as a catalyst. As an organic solvent employed in the reaction, there is effectively employed the solvent which does not react with sultones and has a large polarity and is readily recovered as aforementioned. The acetone-water reaction medium or the methanol-water reaction medium, which can make the reaction system uniform, is suitably employed.

The end product is a hygroscopic white solid which discolors at high temperature and does not indicate a sharp melting point. Completion of the reaction is confirmed by an ester value and an infrared spectrum of the product. As a result of sulfonation, while the absorption band at 1600 cm.$^{-1}$ due to carboxylate group which is characteristic absorption of alkali metal salt of monoalkylmaleate decreases, the absorption band at 1730 cm.$^{-1}$ due to ester group increases relatively and the absorption bands at 1200 cm.$^{-1}$ and 1050 cm.$^{-1}$ due to sulfonate emerge.

By the above-mentioned preparation method, sulfoalkyl-alkylmaleate is advantageously prepared in high yield in the absence of polymerization inhibitor such as hydroquinone without by-producing a homopolymer of maleic anhydride, monoalkylmaleate or sulfoalkyl-alkylmaleate since none of maleic anhydride, monoalkylmaleate and sulfoalkyl-alkylmaleate heat-polymerize independently and also catalytically polymerize independently under a normal preparation condition.

On the other hand, a conventional polymerizable anionic emulsifying agent such as sulfomethylene-α-methyleneacrylate derivatives or monoalkylitaconoxy-propanesulfonate derivatives can heat-polymerize independently. In case of preparing such an emulsifying agent, homopolymer of emulsifying agent is by-produced in large quantities and the yield of the desired product is extremely lowered. Further, in case of adding a large amount of heat-polymerization inhibitor into the reaction system for the purpose of raising the yield, a purification step by some means, that is, a removing step for the inhibitor is required after initiating the reaction. However, there is no purification method advantageous in industry and a great expense is incurred by purification and further a purification efficiency is still insufficient.

The polymerizable anionic emulsifying agent of the invention is prepared in high purity since the reaction of maleic anhydride and higher alcohol proceeds quantitatively. On the contrary, the purity of a conventional polymerizable anionic emulsifying agent is low to some extent. For instance, in case of monoalkylitaconoxy-propanesulfonate derivatives, dialkylitaconate is by-produced in the reaction of preparing monoalkylitaconate from itaconic acid and higher alcohol since a reaction catalyst is employed and a reaction equilibrium is shifted to the production system by dehydration.

Furthermore, maleic anhydride employed in the invention is cheaper than itaconic acid in commercial base. Therefore, there is advantage that the present polymerizable anionic emulsifying agent is prepared in high yield and high purity by the employment of the cheaper starting material.

HLB of the present sulfoalkyl-alkylmaleates, that is, hydrophilic-lipophilic balance of the emulsifying agent can be adjusted by adequately selecting $-(CH_2)_n-SO_3M$ of hydrophilic sulfoalkyl group and R of lipophilic alkyl group. The structure of these substituent groups is determined in accordance with the kind of monomer dispersed in the aqueous medium or the use of polymer since monomer is copolymerized together with the polymerizable anionic emulsifying agent. The carbon number of the alkyl group R is suitably selected from the range of 6 to 22. In case the carbon number of the alkyl group R is less than 6 or more than 22, the emulsifying agent hardly shows a hydrophilic-lipophilic balance suitable for the emulsion polymerization.

The polymerizable anionic emulsifying agent of the invention is added into an emulsion polymerization system to make emulsion polymerization proceed the same as in a normal nonpolymerizable emulsifying agent. The polymerizable anionic emulsifying agent per se is also copolymerized with monomer and chemically bonded within a polymer molecule. Then, the residual amount of the emulsifying agent is infinitesimal when the polymerization terminates. Therefore, it is possible to minimize the discharge of environmental pollutants which are discharged together with industrial wastes at the time of separating the polymer from latex through passing salting-out, filtration and washing. In order to exhibit the effect preventing discharge of environmental pollutants most effectively, it is necessary to employ the present polymerizable anionic emulsifying agent according to the following means. That is to say, 93 to 99.5 % by weight of $\alpha,\beta$-ethylenically unsaturated monomer having solubility of not more than 10 % by weight to water at 35°C. and 0 to 2 % by weight of $\alpha,\beta$-ethylenically unsaturated monomer having a solubility of more than 10 % by weight to water at 35°C. must be copolymerized in the presence of 0.5 to 5 % by weight of the present polymerizable anionic emulsifying agent in an aqueous medium.

The polymerizable anionic emulsifying agent in the invention has the similar emulsifying function to a conventional anionic emulsifying agent. The emulsifying agent forms micelle in the aqueous medium by which the monomer is solubilized and the resultant polymer particles are protected by chemically bonding so that a stable polymer dispersion is provided. Table 2 shows the measuring results at 30°C. of the relationship between the critical micelle concentration (CMC), which is one index of emulsifying function, and the surface tension at critical micelle concentration concerning the present polymerizable anionic emulsifying agent with reference of the result in case of sodium dodecylbenzenesulfonate which is one of well known emulsifying agents usually employed.

One of the principal advantages of sulfoalkyl-alkylmaleate of the present invention is that an enviromental pollution due to the drainage can be prevented by the employment of the present polymerizable anionic emulsifying agent under the specific condition. Since sulfoalkyl-alkylmaleate does not copolymerize in excess and does not polymerize alone though it adequately copolymerizes with $\alpha,\beta$-ethylenically unsaturated monomer, the water-soluble copolymerized material being abundant in the emulsifying agent or the homopolymer of the emulsifying agent is scarcely produced and the emulsifying agent is chemically bonded to the polymer in high quantities. Therefore, the emulsifying agent employed in the polymerization is scarcely discharged into the drainage as an unreacted emulsifying agent, a water-soluble polymeric material or a homopolymer when the polymer is recovered from the polymer dispersion through salting out, filtration and washing.

Another principal advantage of the present invention is that the deterioration of quality of the shaped article prepared therefrom can be prevented. In case of manufacturing a shaped article such as film, fiber, or the like, from the polymer prepared by employing a conventional emulsifying agent, the obtained shaped article is inferior in transparency, heat stability, mechanical property, fastness to light, chemical resistance or water resistance since the employed emulsifying agent remains in the polymer with being adsorbed even if water washing of the polymer is carried out with a much amount of water. However, according to the present invention, the polymerizable anionic emulsifying agent is chemically bonded within polymer molecule obtained by the copolymerization since the emulsifying agent can adequately copolymerize with the $\alpha,\beta$-ethylenically unsaturated monomer.

It is further surprising that a modacrylic fiber prepared from a copolymer, in which acrylonitrile is contained in the ratio of 30 to 80 % by weight and the emulsifying agent is copolymerized, is not only superior in heat stability and fastness to light but also well improved.

Table 3 shows a variation of viscosity of the aqueous solution of polymerizable emulsifying agent under the condition of polymerization, which is represented by the falling time measured with the elapse of time by Ostwald's viscosimeter at 50°C. The polymerization of polymerizable emulsifying agents was carried out as follows:

As polymerizable emulsifying agents, sodium sulfopropylcetylmaleate which is one of the present polymerizable emulsifying agent, sodium sulfopropyl-$\alpha$-methylacrylate and sodium monocetylitaconoxypropanesulfonate which are conventional polymerizable emulsifying agents and include 500 p.p.m. of hydroquinone are employed. Each polymerization vessel made by glass was charged with each 10 parts by weight of the above-mentioned emulsifying agents, respectively, and further charged with each 90 parts by weight of deionized water and each 0.5 part by weight of ammonium persulfate, respectively. After replaceing air in the vessels sufficiently by nitrogen gas, the vessels were sealed and shaken for polymerization in a constant temperature bath maintained at 55°C. for 36 hours. A part of the above-mentioned aqueous solutions was respectively taken out with the elapse of time and the viscosity was measured at 50°C.

Table 2

| Emulsifying agent | CMC g./100 ml. of water | Surface tension at CMC dyne/cm. |
|---|---|---|
| Sodium sulfopropyl-2-ethylhexylmaleate | 0.9 | 27 |
| Sodium sulfopropyl-tridecylmaleate | 0.2 | 31 |
| Sodium sulfopropyl-cetylmaleate | 0.4 | 32 |
| Sodium sulfopropyl-eicocylmaleate | 0.3 | 34 |
| Sodium sulfopropyl-butylmaleate (Comparative Example) | More than 5 | — |
| Sodium dodecylbenzenesulfonate (Reference Example) | 0.2 | 32 |

Table 3

| Example No. | Polymerizable emulsifying agent | Falling time by Ostwald's viscosiemter | | | |
|---|---|---|---|---|---|
| | | 0 hr. | 12 hrs. | 24 hrs. | 36 hrs. |
| | | second | | | |
| A | Sodium sulfopropyl-cetylmaleate | 42.1 | 42.4 | 42.0 | 42.3 no variation |
| B | Sodium sulfopropyl-α-methylacrylate | 28.8 | high viscosity, measurement is impossible | transparency, water-soluble polymeric material | |
| C | Sodium monocetylitaconoxy-propanesulfonate | 31.6 | 40.4 | 80.3 slight turbidity | high viscosity, oily material exists |

In case of sodium sulfopropyl-cetylmaleate, there is no increasing of viscosity and it shows that sodium sulfopropylcetylmaleate is not polymerized alone. In case of sodium sulfopropyl-α-methylacrylate, the viscosity becomes considerably high at the time of passing 30 minutes from the initiation of polymerization. The aqueous solution is transparency, and it is clear that a water-soluble high polymer is produced. In case of sodium monocetylitaconoxypropanesulfonate, homopolymerization gradually proceeds after passing through a long induction period, and at the same time the oily material presumed as oligomer is produced. Further, it appears that the induction period varies slightly.

Table 4 shows the result of measurement of the residual amount of polymerizable emulsifying agent in filtrate and wash water and the chemical oxygen demand of the filtrated and the wash water. The polymerization and the measurement were carried out as follows: Each polymerization vessel was charged with each 10 parts by weight of the polymerizable emulsifying agent employed in the above viscosity measurement. Further, 2000 parts by weight of deionized water, 190 parts by weight of acrylonitrile, 4 parts by weight of potassium persulfate and 1.5 parts by weight of sodium bisulfite were added to each vessel. After replacing air in the vessel by nitrogen gas, the vessels were sealed and shaken for polymerization on a constant temperature bath maintained at 40°C. for 3 hours. After polymerization, the unreacted acrylonitrile was removed off by evaporation, and then salting-out and filtration were carried out. The washing of polymer was carried out by 8000 parts by weight of water. The filtrate and the wash water were combined and the chemical oxygen demand was measured by a potassium permanganate-method at 100°C. for 30 minutes in accordance with the provision of JIS K 0102. The residual amount of polymerizable emulsifying agent was determined by a absorptiometric method, in which anionic emulsifying agent salt of Methylene Blue was extracted with chloroform and absorbance of extract was measured by a spectrophotometer and the amount was determined from a previously prepared calibration curve. It is difficult to independently determine the amount of the unreacted polymerizable emulsifying agent and that of the polymerizable emulsifying agent bonded in the water-soluble polymer, and therefore, the figures in Table 4 indicate the apparent amount of the polymerizable emulsifying agent including both emulsifying agents. In case of sodium sulfopropyl-cetylmaleate (Example D), the polymer was obtained in a form of latex. On the contrary, in case of sodium sulfopropyl-α-methylacrylate (Example E) and sodium monocetylitaconoxypropanesulfonate (Example F), the polymers were obtained in a form of slurry. The amount of polymerizable emulsifying agent in filtrate and wash water in Example D was 0.28 part by weight. On the other hand, the amount in Examples E and F was approximately twice of that in Example D. The yields of polymer in three Examples are about the same, but it is assumed that the apparent amount of emulsifying agent in filtrate and wash water in Examples E and F is increased as a result of the formation of the water-soluble homopolymer of emulsifying agent or the water-soluble copolymer since the emulsifying agents in Examples E and F are apt to polymerize compared with that in Example D. The value of chemical oxygen demand in Example D is small, while those in Examples E and F are large. It is assumed that the fact is caused by the presence of water-soluble polymeric materials.

Table 4

| Ex. No. | Polymerizable emulsifying agent | Polymer dispersion | Yield of polymer % | Amount of polymerizable emulsifying agent present in the mixture of filtrate and wash water part by weight | COD of the mixture of filtrate and wash water p.p.m. |
|---|---|---|---|---|---|
| D | Sodium sulfopropyl-cetylmaleate | latex | 96.4 | 0.28 | 14 |
| E | Sodium sulfopropyl-α-methylacrylate | slurry | 95.2 | 0.61 | 51 |
| F | Sodium monocetylitaco-noxypropanesulfonate | slurry | 95.6 | 0.58 | 42 |

For the purpose of preventing the discharge of environmental pollutants, the amount of the polymerizable emulsifying agent may vary according to a kind of monomer or a use of polymer. Usually, the emulsifying agent is employed in the ratio of 0.5 to 5 % by weight to the total amount of polymerizable materials. In case the amount employed is less than 0.5 % by weight, the stable polymer dispersion is hardly obtained. In case the amount employed is more than 5 % by weight, the unreacted polymerizable emulsifying agent increases so that the COD value of drainage substantially becomes large.

According to the present invention, α,β-ethylenically unsaturated monomer applicable to the process employing the present polymerizable emulsifying agent must be one which has at least one unsaturated bond capable of subjecting to addition polymerization and has a solubility of not more than 10 % by weight to water at 35°C. Examples of the α,β-ethylenically unsaturated monomer having a solubility of not more than 10 % by weight to water at 35°C. are ethylene, vinyl cyanides such as acrylonitrile, methacrylonitrile and vinylidene cyanide, styrene and derivatives thereof such as α-methylstyrene, p-methylstyrene or p-methoxystyrene, acrylic esters such as methyl acrylate, ethyl acrylate, butyl acrylate, hexyl acrylate and 2-ethylhexyl acrylate, methacrylic esters such as methyl methacrylate, ethyl methacrylate, butyl methacrylate and 2-ethylhexyl methacrylate, halogen-containing monomers such as α-chloromethyl acrylate, α-chloroethyl acrylate, vinyl chloride, vinylidene chloride, vinyl bromide, vinylidene bromide, vinyl fluoride and vinylidene fluoride, vinyl esters such as vinyl acetate, vinyl propionate or vinyl stearate, vinylpyridines such as 2-vinylpyridine, 4-vinylpyridine and 2-methyl-5-vinylpyridine, vinyl ethers such as methyl vinyl ether, ethyl vinyl ether, butyl vinyl ether, dodecyl vinyl ether and cetyl vinyl ether, N-vinyl- carbazole, vinylfuran, isoprene, chloroprene, isobutylene, 1,3-butadiene, and the like. Such an α,β-ethylenically unsaturated monomer is suitably employed alone or together with α,β-ethylenically unsaturated monomer having a solubility of more than 10 % by weight to water at 35°C., in an amount of 93 to 99.5 % by weight to the total amount of polymerizable materials.

In case α,β-ethylenically unsaturated monomer having a solubility of more than 10 % by weight to water at 35°C. in copolymerized, it is suitably employed in an amount not more than 2 % by weight to the total amount of polymerizable materials. Examples of the α,β-ethylenically unsaturated monomer having a solubility of more than 10 % by weight are acrylamide, N-vinylpyrrolidone, acrylic acid, methacrylic acid, allyl sulfonic acid, methallyl sulfonic acid, p-styrene sulfonic acid, and alkali salts thereof. In case of employing such a monomer in large amount, the copolymer with polymerizable emulsifying agent, which is produced as a by-product, is apt to become water-soluble, and such a water-soluble material is discharged into drainage in comparatively high ratio when the polymer is recovered from the polymer dispersion through salting-out, filtration and washing. For the purpose of preventing the discharge of water-soluble material causing an environmental pollution, the above-mentioned monomer having a strong hydrophilic property is preferably employed in an amount of not more than 2 % by weight to the total amount of polymerizable materials although the amount may also depend on the amount of the polymerizable emulsifying agent existing in the system.

Table 5 shows the results of the polymerization according to the process of the invention. Examples G, H and I illustrate the copolymerization of monomer having a solubility of not more than 10 % by weight to water at 35°C. and the specific polymerizable anionic emulsifying agent. Examples K, L, N and O illustrate the copolymerization of monomer having a solubility of not more than 10 % by weight to water at 35°C. monomer having a solubility of more than 10 % by weight to water at 35°C. and the specific polymerizable anionic emulsifying agent in which monomer having a solubility of more than 10 % by weight to water at 35°C. is employed in excess, and also Examples J and M illustrate the copolymerization of the above three polymerizable materials in which monomer having a solubility of more than 10 % by weight to water at 35°C. is employed in the amount within the above-mentioned range. The copolymerization was carried out as follows: A polymerization vessel was charged with 700 ml of deionized water and 100 g. of mixture of polymerizable materials. After replacing air in the vessel by nitrogen gas, 3 g. of ammonium persulfate and 1 g. of sodium bisulfite were added to the vessel and the copolymerization was carried out at a temperature of 50°C. for 5 hours. After copolymerization was terminated, the pressure within the vessel was reduced with maintaining a temperature of 50°C. so that the residual volatile monomer is removed off by evaporation. Then, to the polymer dispersion was added an aqueous solution of sodium sulfate to salt out the copolymer. After filtration of the copolymer dispersion, the copolymer was washed with 6 liters of water and the filtrate and the wash water were combined.

The amount of emulsifying agent in the combined water consisting of filtrate and wash water was determined by an absorptiometric method, and the chemical oxygen demand was determined by a potassium permanganate-method at 100°C. for 30 minutes in accordance with the provision of JIS K 0102.

TABLE 5

| Example No. | Monomer composition | | Sodium sulfo-propyl-cetyl-maleate | present Yield of polymer g. | Amount of emulsifying agent in the mixture of fitrate and wash water g. | COD of the filtrate and wash water p.p.m. |
| --- | --- | --- | --- | --- | --- | --- |
| | Monomer having a solubility of not more than 10% | Monomer having a solubility of more than 10 % g. | | | | |
| G | Acrylonitrile 96 | — | 4 | 93.2 | 0.21 | 17 |
| H | Methyl methacrylate 96 | — | 4 | 89.5 | 0.24 | 21 |
| I | Vinyl acetate 96 | — | 4 | 93.6 | 0.18 | 19 |
| J | Acrylonitrile 95 | Acrylamide 1 | 4 | 92.4 | 0.30 | 31 |
| K | Acrylonitrile 92 | Acrylamide 4 | 4 | 90.2 | 0.68 | 102 |
| L | Acrylonitrile 92 | Acrylic acid 4 | 4 | 94.0 | 0.71 | 98 |
| M | Methyl methacrylate 95 | Methacrylic acid 1 | 4 | 90.6 | 0.32 | 33 |
| N | Methyl methacrylate 92 | Methacrylic acid 4 | 4 | 91.3 | 0.67 | 94 |

TABLE 5-continued

| Example No. | Monomer composition | | | agent present Yield of polymer g. | Amount of emulsifying mixture of in the mixture of fitrate and wash water g. | COD of the filtrate and wash water p.p.m. |
|---|---|---|---|---|---|---|
| | Monomer having a solubility of not more than 10% | Monomer having a solubility of more than 10 % g. | Sodium sulfo-propyl-cetyl-maleate | | | |
| O | Vinyl acetate 92 | N-vinylpyrrolidone 4 | 4 | 92.8 | 0.65 | 119 |

In case of Examples G, H and I, the residual amount of the employed emulsifying agent in the mixture of filtrate and wash water is a little and it shows that the emulsifying agent is chemically bonded in high yield in the recovered polymer. The chemical oxygen demand of the mixture of filtrate and wash water is also low. The chemical oxygen demand caused by the employed monomer, that is, acrylonitrile, methyl methacrylate or vinyl acetate is a few p.p.m. since the unreacted monomer is substantially removed off by evaporation under a reduced pressure. In case of Examples K, L, N and O, the residual amount of the employed emulsifying agent in the mixture of filtrate and wash water is comparatively much. The chemical oxygen demand of the mixture of filtrate and wash water is extremely high. It is caused by the water-soluble polymeric material and monomer, that is, acrylamide, acrylic acid, methacrylic acid or n-vinylpyrrolidone, which is readily soluble in water and is hardly removed off by evaporation under a reduced pressure. In case of Examples J and M, the residual amount of the employed emulsifying agent in the mixture of filtrate and wash water is a little, and the chemical oxygen demand is also comparatively low. In order to satisfy the condition that emulsifying agent and water-soluble polymeric material causing an environmental pollution are not discharged in filtering and washing drainage, it is essential that $\alpha,\beta$-ethylenically unsaturated monomer to be copolymerized with the present polymerizable emulsifying agent must have a solubility of not more than 10 % by weight to water at 35°C. and, in case $\alpha,\beta$-ethylenically unsaturated monomer having a solubility of more than 10 % by weight to water at 35°C. is further copolymerized, the amount must be not more than 2 % by weight to the total amount of the employed polymerizable materials.

The aqueous emulsion polymerization can be carried out in accordance with a conventional process. For instance, the present polymerizable emulsifying agent is added together with $\alpha,\beta$-ethylenically unsaturated monomer into the aqueous medium. After addition of a known polymerization initiator, the polymerizable materials are usually polymerized at a temperature of 30° to 100°C. with agitation. In that case, of course, it is preferable to previously remove materials interfering with the polymerization such as oxygen by means of evacuation or replacement with inert gas such as nitrogen gas. The above-mentioned aqueous medium means a mixture of water and a small amount of water-miscible organic solvent such as alcohols or ketones. According to the process of the invention, a small amount of usual emulsifying agent may be added in the aqueous medium in addition to the present polymerizable emulsifying agent. In case of daring to add a usual emulsifying agent, however, it is preferably employed in less amount than that employed in a conventional emulsion polymerization process since the polymer dispersion being substantially stable can be obtained only by the present polymerizable emulsifying agent.

As a polymerization initiator, any of water-soluble polymerization initiators are applicable. Examples of the water-soluble polymerization initiator are inorganic peroxides such as hydrogen peroxide, potassium persulfate or ammonium persulfate, organic peroxide such as acetyl peroxide, tert-butyl hydroperoxide, tert-butyl perisobutyrate, tert-butyl peroxypivalate. Also the redox system in which the above-mentioned peroxide is employed together with, for instance, sodium sulfite, reductive sulfoxylic compounds such as formaldehyde-sodium sulfoxylate dihydrate, or ferrous sulfate, may be employed. In accordance with a durability of activity of initiator or an apparent reaction rate of a mixture of polymerizable materials, the polymerization initiator may be introduced by such a way as introducing the initiator at once before initiating the polymerization, periodically introducing a part of initiator or a part of one or both ingredients of a redox system through polymerization, or continuously introducing the initiator in the course of polymerization.

In accordance with the reactivity of monomer or the composition of polymer, $\alpha,\beta$-ethylenically unsaturated monomer and the present polymerizable emulsifying agent may be introduced into the polymerizable materials at once at the time of polymerization, periodically introducing a part of the polymerizable materials through polymerization or continuously introducing a part of the polymerizable materials in the course of polymerization.

The polymerizable anionic emulsifying agent of the invention is also applicable to the graft-copolymerization in the presence of polymer latex.

The polymer dispersion obtained by the process employing the present polymerizable emulsifying agent shows an excellent stability without producing coagula or scale on polymerization vessel in spite of that a usual emulsifying agent is employed in a slight amount or is not employed at all.

By employing the present emulsifying agent, the environmental pollutants such as emulsifying agent or water-soluble polymeric material or water-soluble or oil-soluble oligomer are not discharged at the time of filtering polymer from aqueous medium and washing when a polymer employed as a starting material for shaped article such as synthetic resin, synthetic fiber or synthetic rubber is manufactured. Further, in case of processing the polymer obtained by the instant process to a shaped article such as film, fiber, or the like, the polymer can provide a shaped article superior in transparency, heat stability, mechanical property, fastness to light, impact strength, heat flowability and processing property since the emulsifying agent is chemically bonded within the polymer molecule. Especially, in case the polymerizable emulsifying agent of the invention is chemically bonded within molecule of acrylonitrile copolymer having 30 to 80 % by weight of acrylonitrile content as a result of emulsion polymerization employing the present polymerizable emulsifying agent, a modacrylic fiber prepared therefrom can be well improved in heat stability and fastness to light.

In general, a modacrylic fiber has been prepared from copolymer comprising 30 to 80 % by weight of acrylonitrile, 70 to 20 % by weight of vinyl chloride or vinylidene chloride and 0 to 10 by weight of another comonomer as a modifier. However, such a modacrylic fiber has the disadvantage that heat stability and fastness to light are not appreciably excellent. On the contrary, it has been found that heat stability and fastness to light are improved by copolymerizing the present polymerizable anionic emulsifying agent. Though the amount of the polymerizable emulsifying agent employed in order to improve heat stability and fastness to light is not limited particularly if the amount is not less than 0.5 % by weight to the total amount of polymerizable materials, it is suitably employed in the amount of 0.5 to 5 % by weight to the total amount of polymerizable materials under the consideration that the polymerizable emulsifying agent also functions as a modifier for maintaining luster in boiling water and dyeing ability. In case the amount is more than 5 % by weight, modacrylic fiber is apt to deluster in boiling water and uneven dyeing is apt to occur since a hydrophilic property and an affinity to dyestuff of the modacrylic fiber become too large.

It is not clear at the present time why heat stability and fastness to light of the modacrylic fiber are improved by copolymerizing the present polymerizable emulsifying agent with monomer. However, it may be considered that Zipper Reaction of the conjugated double bonds generated by dehydrochlorination caused by heating of modacrylic fiber is stopped at the neighboring two carbon atoms in the maleic acid unit of the polymerizable emulsifying agent, which takes part in the main chain of copolymer, since the carboxylate groups are bonded to the above-mentioned carbon atoms. Or again, it may be considered that the dehydrochlorination of modacrylic fiber activated by photo energy is prevented by absorption of photo energy by maleic acid derivative unit. In that case, it is clear that the above-mentioned properties are not improved for the reason why the residual amount of the polymerizable emulsifying agent adsorbed physically in produced polymer without chemically bonding in the polymer is least. The heat stability and fastness to light of a modacrylic fiber prepared by employing a conventional polymerizable emulsifying agent are not improved in spite of the least amount of emulsifying agent remaining in the fiber.

For the purpose of improving the heat stability and fastness to light of the modacrylic fiber, the fiber is prepared by employing the polymerizable anionic emulsifying agent of the invention through passing the following steps. Acrylonitrile and vinyl chloride or vinylidene chloride are emulsion-polymerized in the presence of the polymerizable emulsifying agent in an aqueous medium to give an aqueous latex or aqueous slurry containing the acrylonitrile copolymer. In that case, a small amount of another $\alpha,\beta$-ethylenically unsaturated monomer may be copolymerized therewith as occasion demands. Then, the polymer powder is taken out from the obtained aqueous latex or the aqueous slurry through salting-out, filtration, washing and drying. The polymer powder is dissolved in an organic solvent to prepare a spinning solution. As occasion demands, there may be added into the spinning solution a heat stabilizer, an antistatic agent, a fluorescent agent, rust inhibitor, a delustering agent and other additives. Then the spinning solution is introduced into a coagulating bath, which consists of the same organic solvent as employed in the preparation of the spinning solution and water, through a spinning nozzle. The coagulated filament is drawn in the second coagulating bath. Then, the obtained filament is introduced into a washing bath to remove the organic solvent, and successively introduced into a primary-oil bath to raise filament separatability of fiber. Then the obtained filament is dried and heat-drawn in order to provide an excellent mechanical property to the fiber. Further, an annealing for providing dimensional stability under tension or non-tension and a second-oil treatment for improving spinning property are carried out in order. From thus obtained fiber, a modacrylic staple is prepared through crimping and cutting. As occasion demands, the above-mentioned annealing may be carried out in final step.

The polymerization step is the most important step to improve the heat stability and the fastness to light. In order to make the effect exert most favorably, the polymerizable emulsifying agent of the invention must be employed in an amount of not less than 0.5 % by weight to the total amount of the polymerizable materials. In the presence of the present polymerizable emulsifying agent, 30 to 80 % by weight, preferably 35 to 75 % by weight of acrylonitrile, 69.5 to 19.5 % by weight, preferably 64.5 to 29.5 % by weight of vinyl chloride and/or vinylidene chloride and 0 to 3 % by weight of another comonomer are copolymerized. As the above another comonomer, there may be employed the aforementioned $\alpha,\beta$-ethylenically unsaturated monomer having a solubility of more than 10 % by weight to water at 35°C. It is desirable that the produced polymer composition is uniform all through the polymerization. For the purpose of making the polymer composition uniform, the ratio of polymerizable emulsifying agent, acrylonitrile, vinyl chloride or vinylidene chloride and another comonomer in the polymerization system is maintained at the fixed ratio through the polymerization in accordance with each copolymerization reactivity ratio. For instance, since acrylonitrile and sodium sulfopropyl-tridecylmaleate are more reactive than vinyl chloride, a copolymer containing 50 % by weight of acrylonitrile, 2 % by weight of sodium sulfopropyl-tridecylmaleate and 48 % by weight of vinyl chloride is uniformly prepared as follows:

At first, 10 parts by weight of acrylonitrile, 0.3 part by weight of sodium sulfopropyl-tridecylmaleate and 90 parts by weight of vinyl chloride are mixed in an aqueous medium to prepare an emulsion. Then, a monomer mixture consisting of 52 parts by weight of acrylonitrile and 1.7 parts by weight of sodium sulfopropyl-tridecylmaleate is continuously introduced into the polymerization system till the polymer yield is reached to 110 parts by weight. Such a mixing ratio is determined by the well known theoretical equation for terpolymer. In case of copolymerizing acrylonitrile, vinylidene chloride and the polymerizable emulsifying agent, the mixing ratio thereof is also determined by the theoretical equation for terpolymer. However, since their copolymerization reactivity ratios are similar to each other, a copolymer having a uniform composition is obtained only by continuously adding a small amount of acrylonitrile.

As the aqueous medium employed in the copolymerization, a water-organic solvent system can be employed in addition to water. Examples of the water-organic solvent system are water-methanol, water-acetone, water-dimethylformamide, water-dimethylacetamide and water-dimethyl sulfoxide. Concerning copolymerization temperature, polymerization catalyst, polymerization manner such as continuous system or batch system, and another polymerization arts, conventional methods are applicable.

As the organic solvent employed in the preparation of the spinning solution, there are employed acetone, acetonitrile, dimethylformamide, dimethylacetamide, dimethyl sulfoxide, ethylene carbonate and mixtures thereof. A concentration of acrylic copolymer in the spinning solution is normally 15 to 30 % by weight. The spun fiber is drawn 1.3 to 5.0 times to the original in the coagulating bath. The drying and heat-drawing are carried out at a temperature of 90° to 140°C., and the fiber is usually drawn 2 to 4 times to the fiber prior to the heat-drawing. The annealing is carried out at a temperature of 130° to 160°C. The spun fiber is eventually drawn 4 to 12 times to the original. Other known spinning arts also may be applied to the preparation of modacrylic fiber.

The heat stability and the fastness to light of the modacrylic fiber are determined by the following method. The heat stability of the fiber is determined by comparing degree of whiteness between the heat drawn for fiber and the fiber annealed at 150°C. for 10 minutes. The less the difference between them, the better the heat stability. The index of the degree of whiteness is represented by Hunter Yellowness calculated by the following equation.

$$\text{Hunter Yellowness (H.Y.)} = \frac{A/0.8 - B/1.18}{G}$$

A: Reflectivity of the fiber surface by light of about 600 m$\mu$.

G: Reflectivity of the fiber surface by light of about 550 m$\mu$.

B: Reflectivity of the fiber surface by light of about 450 m$\mu$. (MgO standard white surface is employed.)

The reflection is measured by photoelectric photometer SEP-H type made by Nippon Seimitsu Kogaku Kabushiki Kaisha. The less Hunter Yellowness, the better the degree of whiteness of the fiber. Interrelation between the above index and a judgement by the naked eye is close. The fastness to light is measured by fade-o-meter at a temperature of 40° ± 2°C. for 320 hours, and determined by the degree of fading and the retention to tensile strength of the fiber. The degree of fading is estimated in accordance with the following classification.

| Class | Exposing time till fading occurs (hours) |
|---|---|
| 8 | 320 |
| 7 | 160 |
| 6 | 80 |
| 5 | 40 |
| 4 | 20 |
| 3 | 10 |
| 2 | 5 |

-continued

| Class | Exposing time till fading occurs (hours) |
|---|---|
| 1 | 2.5 |

The retention to tensile strength is calculated by the following equation.

$$\text{Retention to Tensile strength (\%)} = \frac{G'}{G} \times 100$$

G: Tensile strength before exposure (g./d.)
G': Tensile strength after exposure (g./d.)

Furthermore, as a result of copolymerizing the polymerizable emulsifying agent of the invention with $\alpha,\beta$-ethylenically unsaturated monomer, adhesiveness such as adhesive strength, peeling strength or heat-sealing is improved when the polymer is employed as an adhesive or coating material, and solubility to organic solvent and printability are improved when the polymer is employed as a powdery paint, and water resistance and miscibility with pigment are improved when the polymer dispersion is employed as an aqueous paint.

The invention is more particularly described and explained by means of the following illustrative Examples, in which all parts and percentages are by weight except as noted.

EXAMPLE 1

Sodium sulfopropyl-laurylmaleate 1-1. Preparation of monolaurylmaleate:

A reactor equipped with an agitator and a reflux condenser was charged with 186.1 g. (1.0 mole) of n-lauryl alcohol and 98.1 g. (1.0 mole) of maleic anhydride. The mixture was heated at a temperature of 80°C. for 2 hours with agitation, and thereafter was allowed to cool. The obtained white solid was recrystallized from hexane to give 270.2 g. of white crystal having a melting point of 56.3° to 56.9°C. and an ester value of 195 (KOH mg./g.). The yield was 95 %.

1-2. Preparation of sodium monolaurylmaleate:

To 142.2 g. (0.5 mole) of the product obtained in the above item 1-1 was added 100 g. of acetone. After agitating the mixture at a temperature of 30° to 50°C. to give a uniform solution, 50 % aqueous solution of sodium hydroxide containing 20 g. of sodium hydroxide was gradually added dropwise to the solution with agitation and with maintaining the reaction temperature at below 58° to 60°C., followed by further agitation for 30 minutes. The reaction mixture was cooled to a temperature of 5°C. and the obtained white suspension was filtered and washed with cold acetone to give 148.6 g. of a white solid having a melting point of 107.8° to 111.2°C. and an ester value of 182 (KOH mg./g.). The yield was 97 %.

1-3. Preparation of sodium sulfopropyl-laurylmaleate:

To 76.6 g. (0.25 mole) of the product obtained in the above item 1-2 were added 50 g. of acetone and 30.5 g. (0.25 mole) of propanesultone. The reaction mixture was agitated for 2 hours at a temperature that acetone could be refluxed. The mixture was cooled to a room temperature. The precipitated white solid was filtered and washed with cold acetone. The obtained hygroscopic white solid was dried under vaccum to give 106.0 g. of sodium sulfopropyl-laurylmaleate having an ester value of 258 (KOH mg./g.). The yield was 99 %.

Infrared spectrums of monolaurylmaleate, sodium monolaurylmaleate and sodium sulfopropyllaurylmaleate were shown in FIGS. 1 to 3, respectively.

EXAMPLE 2

Sodium sulfopropyl-hexylmaleate 2-1. Preparation of sodium monohexylmaleate:

A mixture consisting of 98.1 g. (1.0 mole) of maleic anhydride and 102.1 g. (1.0 mole) of n-hexanol was agitated for 2 hours at a temperature of 80°C. by the same manner as in Example 1, item 1-1. To the obtained uniform, clear liquid of monohexylmaleate (ester value: 275) was added 200 g. of acetone, and a neutralizing reaction was carried out with adding dropwise 50 % aqueous solution of sodium hydroxide by the same manner as in Example 1, item 1-2. Then, the reaction mixture was cooled. The precipitated white solid was filtered and washed with cold acetone to give 211 g. of hygroscopic white solid having a melting point of 49° to 52°C. and an ester value of 249. The yield of sodium monohexylmaleate was 95 %. 2-2. Preparation of sodium sulfopropyl-hexylmaleate:

The same procedure as in Example 1, item 1-3 was repeated except that 55.6 g. of the product obtained in the above item 2-1 was employed. The obtained hygroscopic white solid was dried to give 84.4 g. of sodium sulfopropyl-hexylmaleate having an ester value of 320. The yield was 98 %.

Infrared spectrums of monohexylmaleate, sodium monohexylmaleate and sodium sulfopropyl-hexylmaleate were shown in FIGS. 4 to 6, respectively.

EXAMPLE 3

Sodium sulfopropyl-cetylmaleate 3-1. Preparation of monocetylmaleate:

A reactor equipped with an agitator and a reflux condenser was charged with 242.2 g. (1.0 mole) of n-cetyl alcohol and 98.1 g. (1.0 mole) of maleic anhydride. The mixture was heated at a temperature of 80°C. for 2 hours with agitation, and thereafter was allowed to cool. The product was recrystallized from hexane to give 326.7 g. of white solid having a melting point of 77.4° to 79.0°C. and ester value of 160. The yield was 96 %.

3-2. Preparation of sodium monocetylmaleate:

To 170.2 g (0.5 mole) of the product obtained in the above item 3-1 was added 100 g. of acetone, and the mixture was agitated. Then, the neutralizing reaction was carried out by adding dropwise 30 % aqueous solution of sodium hydroxide containing 20 g. of sodium hydroxide to the obtained uniform solution to give 87.9 g. of white solid having a melting point of 113.9° to 115.8°C. and an ester value of 148. The yield of sodium monocetylmaleate was 97 %. 3-3. Preparation of sodium sulfopropyl-cetylmaleate:

To 90.6 g. (0.25 mole) of the product obtained in the above item 3-2 was added 50 g. of acetone. After agitating the mixture at 55° to 60°C, 30.5 g. (0.25 mole) of propanesultone was further added and thus obtained mixture was refluxed for 2 hours with heating. Then, the mixture was cooled to a room temperature and the precipitated white solid was washed with cold acetone. Thus obtained hygroscopic white solid was dried under vaccum to give 119.9 g. of sodium sulfopropyl-cetylmaleate having an ester value of 228. The yield was 99 %.

Infrared spectrums of monocetylmaleate, sodium monocetylmaleate and sodium sulfopropyl-cetylmaleate were shown in FIGS. 7 to 9, respectively.

EXAMPLE 4

Sodium sulfopropyl-cetylmaleate

A reactor equipped with an agitator and a reflux condenser was charged with 242.2 g. (1.0 mole) of n-cetyl alcohol and 23 g. (1.0 mole) of metallic sodium. The mixture was heated at a temperature of 120°C. for 5 hours with agitation to prepare sodium cetylate. Then, the obtained sodium cetylate was gradually added with agitation to a solution which was obtained by dissolving 98.1 (1.0 mole) of maleic anhydride in 500 g. of benzene at a temperature of 60°C. After addition, the mixture was futher agitated at a temperature of 80°C. for 2 hours. The reacted mixture was cooled, and the obtained white precipitate was filtered and dried under vaccum to give 261.4 g. of sodium monocetylmaleate having a melting point of 115.3° to 115.8°C. and an ester value of 150. The yield was 97 %.

Then, from thus obtained sodium monocetylmaleate, sodium sulfopropyl-cetylmaleate was prepared by the same manner as in Example 3, item 3-3.

EXAMPLE 5

Sodium sulfopropyl-laurylmaleate

To 71.1 g. (0.25 mole) of monolaurylmaleate obtained by the procedure of Example 1, item 1-1 was added to 50 g. of isopropanol. After agitation, a suspension containing 10 g. (0.25 mole) of sodium hydroxide in 250 g. of isopropanol was added to the mixture and thus obtained mixture was refluxed at a temperature of 80°C. for 1.5 hours with agitation. Then, the reacted mixture was added with 30.5 g. (0.25 mole) of propanesultone and was further agitated at a temperature of 80°C. for 2 hours. From the obtained white gelatinous liquid, isopropanol was distilled off under reduced pressure and thereafter the vacuum drying was carried out to give 106.0 g. of white waxy sodium sulfopropyl-laurylmaleate having an ester value of 255. The yield was 99 %.

EXAMPLE 6

Sodium sulfopropyl-laurylmeleate

To 71.1 g. (0.25 mole) of monolaurylmaleate obtained by the procedure of Example 1, item 1-1 was added 100 g. of water, and thereto 20 % aqueous solution containing 10 g. of sodium hydroxide was gradually added dropwise with maintaining a reaction temperature below 55°C. Then the mixture was agitated at a temperature of 40°C. for 0.5 hour, and thereto 30.5 g. (0.25 mole) of propanesultone was added. The reaction mixture was agitated at a temperature of 60°C for 2 hours, and after reaction, water was distilled off under a reduced pressure from the obtained white gelatinous product. The vacuum drying was carried out to give 105.0 g. of hygroscopic white solid of sodium sulfopropyl-laurylmaleate having an ester value of 256. The yield was 98 %.

EXAMPLE 7

Sodium sulfoethyl-laurylmaleate

To 71.1 g. (0.25 mole) of monolaurylmaleate obtained by the procedure of Example 1, item 1-1 was added 40.6 g. (0.25 mole) of sodium 2-oxy-ethanesulfonate. The mixture was agitated at a temperature of 220°C. for 1.5 to 2 hours with removing water produced during the reaction under a reduced pressure of 15 to 300 mmHg. Then the mixture was cooled to a room temperature, and 82.9 g. of white waxy sodium sulfoethyl-laurylmaleate having an ester value of 210 was obtained. The yield was 80 %. The melting point was indefinite since the product had a thermal decomposing property.

EXAMPLE 8

Sodium sulfoethyl-laurylmaleate

The mixture of 71.1 g. (0.25 mole) of monolaurylmaleate obtained by the procedure of Example 1, item 1-1 and 40.6 g. (0.25 mole) of sodium 2-oxy-ethanesulfonate was agitated at a temperature for about 8 to 10 hours with passing hydrogen chloride gas till the obtained reaction product became soluble in water. To the reaction product were added 200 g. of ice water and 100 g. of saturated solution of sodium chloride. After allowing it to stand, the upper layer was separated off to give the under layer containing sulfoethyl-laurylmaleate. The under layer was neutralized by 10 % aqueous solution of sodium hydroxide, then water was removed off under reduced pressure to give 80.8 g. of white waxy sodium sulfoethyl-laurylmaleate having an ester value of 230. The yield was 78 %.

EXAMPLE 9

Sodium sulfobutyl-laurylmaleate

To acetone was added 76.6 g. (0.25 mole) of sodium monolaurylmaleate obtained by the procedure of Example 1, item 1-2, and dissolved. Then, 34.1 g. (0.25 mole) of butanesultone was added to the solution, and the mixture was agitated at a temperature of 60°C. for 3 hours. The reacted mixture was cooled to a room temperature and the precipitated white gelatinous solid was washed with cold acetone. The obtained hygroscopic white solid was dried under vaccum to give 105.2 g. of sodium sulfobutyl-laurylmaleate having an ester value of 240. The yield was 95 %.

EXAMPLES 10 TO 15 AND COMPARATIVE EXAMPLES 1 TO 6

Practical Example (I) of the polymerization process for preventing environmental pollutions A reactor equipped with an agitator and a reflux condenser was charged with 200 ml. of toluene, 242 g. of cetyl alcohol and 5 ml. of 5 % aqueous solution of sulfuric acid. After substantial agitation, 98 g. of maleic anhydride was added and the mixture was refluxed at a temperature of 105° to 110°C. for 4 hours. Then the mixture was gradually cooled to a temperature of 0°C. and the precipitated white crystal was filtered with suction. The crystal was recrystallized from the mixed solvent to benzene-ligroin to give about 326 g. of monocetyl maleate. Another reactor equipped with an agitator and a reflux condenser was charged with 150 ml. of isopropyl alcohol and 300 g. of monocethyl maleate. The reactor was further charged with a suspension in which 40 g. of sodium hydroxide is suspended in 350 ml. of isopropyl alcohol with agitation and the refluxing was started with heating. Then the mixed solution of 100 ml. of isopropyl alcohol and 108 g. of propanesultone was gradually added and the mixture was refluxed at a temperature of 78° to 82°C. for 4 hours with agitation. After the reaction was terminated, isopropyl alcohol was removed off by reducing the pressure with heating. Finally the resultant was dried at a temperature of 105° to 110°C. to give about 417 g. of a white waxy material of sodium sulfopropylcetyl maleate.

Thus obtained sodium sulfopropylcetyl maleate was employed as a polymerizable emulsifying agent and an aqueous emulsion polymerization was carried out as follows: A pressure polymerization vessel was charged with 560 ml. of deionized water, 3 g. of sodium sulfite, 0.002 g. of ferrous sulfate and 100 g. of monomer mixture as shown in Table 6. With agitating the mixture and elevating the temperature 0.5 g. of ammonium persulfate was added to the mixture and the polymerization was carried out at a temperature of 50°C. Ammonium persulfate was added in an amount of 0.2 g. at intervals of an hour. In each Example, the polymerization was continued for about 5 to 8 hours till the yield became more than 90 %. After the polymerization was terminated, the vessel was evacuated with maintaining the temperature at 50°C. so that the unreacted volatile monomer was removed off from the obtained polymer dispersion. Then 100 ml. of a 10 % aqueous solution of sodium sulfate was added to the polymer dispersion to salt out the polymer. After heating, the polymer dispersion was filtered and the polymer was sufficiently washed with 3.5 liters of water.

The filtrate and the wash water were combined, and the amount of the emulsifying agent present in the combined water was determined by a absorptiometric method and the chemical oxygen demand of the combined water was determined by a potassium permanganate-method at 100°C. for 30 minutes in accordance with the provision of JIS K 0102-1971. The term transparency of film refers to the percent transmission which is determined by measuring the ratio of light transmitted through the film having a thickness of 0.3 mm. prepared from a 15 % tetrahydrofuranmethyl ethyl ketone solution of the polymer under the prescribed condition. Further, the term heat stability of film refers to the time required until the color of the above-mentioned film turns to light brown when the film is heated at a temperature of 150°C. in Geer's oven.

The results were shown in Table 6.

Table 6

| Example No. | Monomer composition | | | | Emulsifying agent | | Yield of polymer | Amount of emulsifying agent present in the mixture of filtrate and wash water | COD of the mixture of filtrate and wash water | Property of the film | |
|---|---|---|---|---|---|---|---|---|---|---|---|
| | Vinyl chloride | Vinyl acetate | N-vinyl-pyrrolidone | Sodium sulfopropyl-cetyl-maleate | Sodium dodecylbenzene sulfonate | Sodium lauryl sulfate | | | | Transparency | Heat stability |
| | % | | | | % | | g. | g. | p.p.m. | % | min. |
| 10 | 89.3 | 10 | — | 0.7 | — | — | 92.0 | 0.04 | 6 | 92 | 35 |
| 11 | 88 | 10 | — | 2 | — | — | 93.3 | 0.09 | 11 | 93 | 40 |
| 12 | 86 | 10 | — | 4 | — | — | 93.6 | 0.18 | 20 | 95 | 45 |
| 13 | 87 | 10 | 1 | 2 | — | — | 94.3 | 0.13 | 18 | 94 | 40 |
| 14 | 86 | 10 | 2 | 2 | — | — | 94.5 | 0.18 | 21 | 94 | 40 |
| 15 | 85 | 10 | 1 | 4 | — | — | 91.9 | 0.22 | 23 | 95 | 45 |
| Com. Ex. 1 | 89.7 | 10 | — | 0.3 | — | — | large quantity of coagula | — | — | 86 | 25 |
| 2 | 82 | 10 | — | 8 | — | — | 92.8 | 0.56 | 64 | 91 | 40 |
| 3 | 84 | 10 | 4 | 2 | — | — | 92.0 | 0.35 | 61 | 92 | 35 |
| 4 | 82 | 10 | 4 | 4 | — | — | 93.5 | 0.59 | 97 | 92 | 35 |
| 5 | 90 | 10 | — | — | 2 | — | 92.6 | 1.89 | 52 | 82 | 25 |
| 6 | 90 | 10 | — | — | — | 2 | 91.7 | 1.92 | 85 | 84 | 25 |

As is clear from Table 6, the amount of polymerizable emulsifying agent in the mixture of filtrate and wash water in Examples 10 to 15 was a little and the chemical oxygen demand was also low. Therefore, the filtrate and the wash water can be discharged as an industrial waste without any treatment. Also, the transparency and the heat stability of the film were excellent. On the other hand, in case of Comparative Example 1, the uniform polymer dispersion was not obtained as a result of the formation of a large amount of coagula due to the lack of the polymerizable emulsifying agent. In case of Comparative Example 2, the unreacted polymerizable emulsifying agent was abundantly present in the filtrate and the wash water and the chemical oxygen demand was also high since the polymerizable emulsifying agent was employed in excess. In case of Comparative Examples 3 and 4, the water-soluble polymeric material was by-produced since N-vinylpyrrolidone being readily soluble in water was employed in large quantities. As a result, the amount of polymerizable emulsifying agent in the mixture of filtrate and wash water and the chemical oxygen demand are high, and the filtrate and the wash water can not be discharged as an industrial waste without any treatment. Comparative Examples 5 and 6 show the polymerization employing a conventional non-polymerizable emulsifying agent. A large portion of the employed emulsifying agent was present in the filtrate and the wash water, and the chemical oxygen demand was also high. Further, the transparency and the heat stability of the film were inferior. It is assumed that the inferiority is caused by the emulsifying agent adsorbed into the polymer.

EXAMPLES 16 TO 21 AND COMPARATIVE EXAMPLES 7 TO 12

Practical Example (II) of the polymerization process for preventing environmental pollutions Sodium sulfopropyl-2-ethylhexylmaleate was prepared by the same manner as in Example 10 and was employed as a polymerizable emulsifying agent.

A stainless steel polymerization vessel was charged with 600 ml. of deionized water, 0.7 g of ammonium persulfate and 300 g. of monomer mixture as shown in Table 7. After replacing air in the vessel with nitrogen gas, the polymerization was carried out at a temperarure of 50°C. for 20 hours. Then steam was blown through the obtained latex so that the unreacted monomer was substantially removed off. The salting-out was carried out with 10 % aqueous solution of zinc chloride. After filtration, the polymer was substantially washed with 6.6 liters of water and dried.

Then the amount of polymerizable emulsifying agent and the chemical oxygen demand were measured by the same manner as in Example 10.

Further, the processing property of the polymer was evaluated by a mixing roll for rubber at a temperature of 40° to 60°C. The processing property is determined by the degree of winding to roll and the condition of polymer according to the following criterion.

A: smooth winding on roll and extremely easy mixing

B: winding on roll without separating from roll and easy mixing but a little bad eating into roll C: easy separation from roll and not easy mixing As Comparative Examples 7 to 12, the same procedures as in the above Examples were repeated except that sodium dodecylbenzenesulfonate was employed instead of the polymerizable emulsifying agent.

The results were shown in Table 7.

Table 7

| Example No. | Monomer composition | | | | | | | | Emulsifying agent |
|---|---|---|---|---|---|---|---|---|---|
| | Ethyl acrylate | Acrylonitrile | Divinyl-benzene | Fumalic acid | Monobutyl itaconate | Methacrylic acid | Acrylic acid | Sodium sulfopropyl-2-ethylhexyl-maleate | Sodium dodecylbenzene sulfonate |
| | part | | | | | | | | part |
| 16 | 90 | 10 | 0.5 | 2 | — | — | — | 3 | |
| 17 | 90 | 10 | 0.5 | 5 | — | — | — | 3 | |
| 18 | 90 | 10 | 0.5 | — | 2 | — | — | 3 | |
| 19 | 90 | 10 | 0.5 | — | 5 | — | — | 3 | |
| 20 | 90 | 10 | 0.5 | — | — | 2 | — | 3 | |
| 21 | 90 | 10 | 0.5 | — | — | — | 2 | 3 | |

Table 7-continued

| | | | | | | | | | | |
|---|---|---|---|---|---|---|---|---|---|---|
| Com. Ex. 7 | 90 | 10 | 0.5 | — | — | 5 | — | 3 | — | |
| 8 | 90 | 10 | 0.5 | — | — | — | 5 | 3 | — | |
| 9 | 90 | 10 | 0.5 | 5 | — | — | — | 7 | — | |
| 10 | 90 | 10 | 0.5 | — | 5 | — | — | 7 | — | |
| 11 | 90 | 10 | 0.5 | — | 2 | — | — | — | 3 | |
| 12 | 90 | 10 | 0.5 | — | 5 | — | — | — | 3 | |

| Yield of polymer | Amount of polymerizable emulsifying agent present in the mixture of filtrate and wash water | Amount of emulsifying agent present in the mixture of filtrate and wash water | COD of the mixture of filtrate and wash water | Processing property of the acrylic rubber by mixing roll |
|---|---|---|---|---|
| g. | g. | g. | p.p.m. | — |
| 286 | 0.31 | — | 21 | A |
| 288 | 0.32 | — | 28 | A |
| 285 | 0.29 | — | 20 | A |
| 292 | 0.28 | — | 26 | A |
| 290 | 0.38 | — | 26 | A |
| 287 | 0.36 | — | 27 | A |
| 278 | 0.81 | — | 92 | B |
| 276 | 0.76 | — | 88 | B |
| 271 | 0.89 | — | 72 | B |
| 273 | 0.84 | — | 70 | B |
| 290 | — | 8.12 | 113 | B |
| 286 | — | 8.27 | 125 | C |

As is clear from Table 7, the amount of polymerizable emulsifying agent in the mixture of filtrate and wash water in Examples 16 to 21 is small and the chemical oxygen demand is also low. Therefore, the filtrate and the wash water can be discharged as an industrial waste without any treatment. Morevoer, the processing property of the obtained acrylic-rubbers is favorable. In case of Comparative Examples 7 and 8, water-soluble polymeric material is by-produced since methacrylic acid or acrylic acid being readily soluble in water is employed in large quantities. As a result, the amount of polymerizable emulsifying agent and the chemical oxygen demand are high, and the filtrate and the wash water can not be discharged as an industrial waste without any treatment. In case of Comparative Examples 9 to 10, the filtrate and the wash water are not clean as a result of employing the polymerizable emulsifying agent in large quantities. In case of Comparative Examples 11 and 12, a conventional non-polymerizable emulsifying agent is employed and a large portion of the employed emulsifying agent is discharged in the filtrate and the wash water. Moreover, the chemical oxygen demand is high. Further, the processing property of the acrylic rubber obtained in Comparative Examples is a rather poor, especially that in Comparative Example 12 is inferior.

EXAMPLES 22 TO 25 AND COMPARATIVE EXAMPLES 13 TO 14

Practical Example (III) of the polymerization process for preventing environmental pollutions Sodium sulfopropyl-tridecylmaleate was prepared by the same manner as in Example 10 and was employed as a polymerizable emulsifying agent.

A pressure polymerization vessel made by stainless steel was charged with 1500 ml. of deionized water, 3 g. of sodium bicarbonate, 30 g. of potassium persulfate and sodium sulfopropyltridecylmaleate of the amount shown in Table 8. After removing air in the vessel by evacuation, 300 g. of the monomer mixture of vinyl chloride, ethylene and isobutylene of which composition was shown in Table 8 was added to the vessel and the polymerization was carried out at a temperature of 47°C. for 30 hours. Then the obtained latex was taken out and the salting out was done with a 10 % aqueous solution of sodium chloride. After heating at a temperature of 80°C. with agitation, the polymer was filtered and washed with 9.7 liters of hot water and dried.

The amount of emulsifying agent in the mixture of filtrate and wash water and the chemicl oxygen demand of the mixture were determined by the same manner as in Example 10. Further, the heat stability and the heat flowability of the polymer were determined.

The heat stability was measured as follows: To 100 parts of the polymer were added 0.5 part of lead stearate and 1.7 parts of dibutyl tin maleate. The compound was mixed by a mixing roll at a temperature of 150°C. for 10 minutes and a sheet having a thickness of 1 mm. was prepared. The sheet was heated at a temperature of 180°C. in Geer's oven and the time till the color of the sheet turns to dark brown was measured. The heat stability was represented by thus measured time.

The heat flowability was measured as follows: A sheet was prepared by the same manner as in the above measurement and pelletized, The pellet was packed in a Koka flow tester equipped with a nozzle having a diameter of 1 mm. and a length of 10 mm. The temperature of the flow tester was elevated at a rate of 6°C./min. under a pressure of 200 kg./cm.$^2$, and the temperature was measured when the flow rate from the nozzle became 2 mm.$^3$/min. The heat flowability was represented by thus measured temperature.

The detailed explanation of Koka flow tester is described in Teikichi Arai's "A Guide to the Testing of Rheological Properties with Koka Flow Tester" published by Maruzen Co., Ltd. (1958).

As Comparative Examples 13 and 14, the same procedures as in the above Examples were repeated except that sodium lauryl suflate was employed instead of the polymerizable emulsifying agent.

The results were shown in Table 8.

Table 8

| Example No. | Monomer composition | | | | Emulsifying agent | Yield of polymer | Amount of polymerizable emulsifying agent present in the mixture of filtrate and wash water | Amount of emulsifying agent present in the mixture of filtrate and wash water | COD of the mixture of filtrate and wash water | Property | |
|---|---|---|---|---|---|---|---|---|---|---|---|
| | Vinyl chloride | Ethylene | Isobutylene | Sodium sulfopropyltridecylmaleate | Sodium lauryl sulfate | | | | | Heat stability | Heat flowability |
| | part | | | | part | g. | g. | g. | p.p.m. | min. | °C. |
| 22 | 85 | 10 | 5 | 2 | — | 264 | 0.31 | — | 13 | 120 | 119 |
| 23 | 85 | 10 | 5 | 4 | — | 276 | 0.58 | — | 24 | 130 | 113 |
| 24 | 80 | 10 | 10 | 2 | — | 268 | 0.27 | — | 12 | 120 | 115 |
| 25 | 80 | 10 | 10 | 4 | — | 270 | 0.59 | — | 23 | 130 | 108 |
| Com. Ex. 13 | 85 | 10 | 5 | — | 3 | 263 | — | 8.42 | 138 | 90 | 130 |
| 14 | 80 | 10 | 10 | — | 3 | 260 | — | 8.34 | 126 | 90 | 125 |

As is clear from Table 8, the amount of polymerizable emulsifying agent in the mixture of filtrate and wash water in Examples 22 to 25 is low and the chemical oxygen demand of the mixture is also low. Therefore, the filtrate and the wash water can be discharged as an industrial waste without any treatment. A conventional non-polymerizable emulsifying agent is employed in Comparative Examples 13 and 14, and a large portion of the employed emulsifying agent is discharged in the filtrate and the wash water. Moreover, the chemical oxygen demand is high. These may cause an environmental pollution. Further, the polymers obtained in Examples 22 to 25, in which the polymerizable emulsifying agent is chemically bonded within the polymer molecule, can give a sheet improved in heat stability and a pellet improved in heat flowability. On the other hand, the polymers obtained in Comparative Examples 13 and 14 are inferior in heat stability and it is assumed that the inferiority is caused by the emulsifying agent adsorbed into the polymer.

EXAMPLE 26 AND COMPARATIVE EXAMPLES 15 TO 16

Practical Example (IV) of the polymerization process for preventing environmental pollutions A pressure polymerization vessel made by stainless steel was charged with one liter of deionized water, 30 g. of sodium sulfobutyl-tridecylmaleate, 10 g. of ammonium persulfate, 5 g. of sodium sulfate, 2 g. of dodecyl mercaptan, 80 g. of methyl methacrylate, 620 g. of butadiene and 300 g. of styrene. The polymerization was carried out at a temperature of 63°C. for 12 hours and further at a temperature of 83° for 12 hours. The yield of polymer was 97 %.

To thus obtained latex were added 1.6 liters of deionized water, 33 g. of sodium sulfobutyl-tridecylmaleate and 3 g. of ammonium persulfate, and the mixture was uniformly agitated. A polymerization vessel was continuously charged with the above diluted latex and a monomer mixture consisting of 400 g. of methyl methacrylate, 400 g. of styrene and 3 g. of dodecyl mercaptan by a fixed rating pump in the course of polymerization. The polymerization was carried out at a temperature of 70°C. for 6 hours of average residence time and the latex was continuously taken out. To the latex taken out was added a 10 % aqueous solution of sodium chloride to salt out graft-copolymer, and after heat treatment, the graft-copolymer was filtered and washed with 31 liters of hot water of 50°C. and dried.

The amount of polymerizable emulsifying agent in the mixture of filtrate and wash water and the chemical oxygen demand of the mixture were determined by the same manner as in Example 10.

Further, the obtained graft-copolymers were finely divided and blended with polyvinyl chloride (straight polymer, $\bar{P} = 1000$), and from which the test samples for Izot impact test and measurement of percent transmission were prepared as follows: To 100 parts of polyvinyl chloride were added 15 parts of the graft-copolymer, 1.5 parts of dibutyl tin mercaptide, 1.0 part of dibutyl tin maleate and 0.5 part of butyl stearate. The mixture was blended by a ribbon blender for 5 minutes, then extruded from an extruder at a screw speed of 45 r.p.m. and at a temperature of 190°C. to prepare pellets. A test sample was prepared from the pellet by pressing for 10 minutes at a temperature of 190°C. under a pressure of 200 kg./cm²., and Izot impact strength and percent transmission were measured according to the provision of JIS K 6871 and ASTM-D1003, respectively.

As Comparative Examples 15 and 16, the same procedures as in the above Example were repeated except that sodium lauryl sulfate was employed instead of the polymerizable emulsifying agent.

The results were shown in Table 9.

Table 9

| Example No. | Emulsifying agent | | | | Amount of polymerizable emulsifying agent present in the mixture of filtrate and wash water | Amount of emulsifying agent present in the mixture of filtrate and wash water | COD of the mixture of filtrate and wash water | Property | |
|---|---|---|---|---|---|---|---|---|---|
| | Amount employed in the batchwise polymerization in the first half | | Amount employed in the continuous polymerization in the second half | | | | | Izot impact strength | Percent transmission |
| | Sodium sulfobutyl-tridecylmaleate | Sodium lauryl sulfate | Sodium sulfobutyl-tridecylmaleate | Sodium lauryl sulfate | | | | | |
| | g. | | | | g. | g. | p.p.m. | kg. cm./cm. | % |
| 26 | 30 | — | 33 | — | 1.9 | — | 28 | 60 | 93 |
| Com. Ex. 15 | — | 20 | — | 33 | — | 49.2 | 290 | 50 | 88 |

Table 9-continued

| Example No. | Emulsifying agent | | | | Amount of polymerizable emulsifying agent present in the mixture of filtrate and wash water | Amount of emulsifying agent present in the mixture of filtrate and wash water | COD of the mixture of filtrate wash water | Property | |
|---|---|---|---|---|---|---|---|---|---|
| | Amount employed in the batchwise polymerization in the first half | | Amount employed in the continuous polymerization in the second half | | | | | Izot impact strength | Percent transmission |
| | Sodium sulfobutyl-tridecylmaleate | Sodium lauryl sulfate | Sodium sulfobutyl-tridecylmaleate | Sodium lauryl sulfate | | | | | |
| | g. | | | | g. | g. | p.p.m. | kg. cm./cm. | % |
| 16 | — | 5 | — | 25 | — | 27.8 | 156 | 5 | 82 |

A particle size of polymer in the latex, which was obtained by the batchwise polymerization in the first half in Example 26 and Comparative Examples 15 and 16, was 0.10 μ, 0.11 μ and 0.15 μ, respectively. It appears that the improvement in impact strength and transparency of shaped article prepared from the compound of the graft-copolymer and polyvinyl chloride is closely connected with the particle size of polymer of the above-mentioned latex.

The amount of polymerizable emulsifying agent in the mixture of filtrate and wash water in Example 26 is a little and the chemical oxygen demand of the mixture is also low. Moreover, the impact strength and the transparency are excellent. For the purpose of obtaining a polymer having excellent impact strength and transparency nearly equal to that in Example 26, the particle size of polymer in Comparative Example 15 is adjusted from the view point of connection between a particle size and properties, in which a conventional non-polymerizable emulsifying agent is employed. However, the transparency in Comparative Example 15 is poorer than that in Example 26. It is one of causes by which a small amount of the emulsifying agent is adsorbed by the graft-copolymer. Further, the amount of emulsifying agent in the mixture of filtrate and wash water in Comparative Example 15 is much and the chemical oxygen demand is also high. For the purpose of reducing the amount of emulsifying agent discharged with drainage, Comparative Example 16 is carried out by employing a conventional non-polymerizable emulsifying agent in less amount. However, the particle size of the obtained polymer becomes too large, and as a result, the impact strength extremely lowers. It also makes the transparency worse. In spite of the employment in less amount, the amount of emulsifying agent in the mixture of filtrate and wash water in Comparative Example 16 is much and the chemical oxygen demand of the mixture is also high.

EXAMPLES 27 TO 31 AND COMPARATIVE EXAMPLES 17 TO 21

Improved modacrylic fiber
[Preparation of acrylic copolymer]

A pressure polymerization vessel made by stainless steel was charged with 10 liters of deionized water containing 1 p.p.m. of ferrous sulfate, 7 g. of sodium bisulfate and 14 g. of sulfurous acid. Then, 2000 g. of composition for initial charging shown in Table 10 was added to the vessel and the temperature was elevated to 40°C. with agitation. After elevating the temperature, 1 g. of ammonium persulfate dissolved in a small amount of water was added to initiate the polymerization. At the same time as the initiation of polymerization, an aqueous solution of ammonium persulfate was continuously introduced to the vessel so as to provide ammonium persulfate at the rate of 1 g./hr. The polymerization was carried out for about 5 hours till the polymer yield reached to about 2000 g. During the polymerization, a composition for continuous charging shown in Table 10 was continuously introduced to the vessel to make the obtained copolymer composition uniform. Salting-out was carried out by adding to the obtained latex a 20 % aqueous solution of sodium chloride in an amount of ⅛ time to the latex. The mixture was heated to a temperature of 90°C. to precipitate the copolymer in slurry. Then filtration, washing and drying were carried out to give a powdery acrylic copolymer.

The copolymer composition shown in Table 10 was determined by elemental analysis to nitrogen, chlorine, and, as occasion demands, sulfur.

In case of Examples 27 and 28 and Comparative Example 17, sodium dodecylbenzenesulfonate of a usual emulsifying agent was employed together with the present polymerizable emulsifying agent in order to increase the stability of latex since sodium sulfopropyllaurylmaleate was employed in a comparatively small amount.

[Preparation of modacrylic fiber]

To 335 parts of acetone were added 100 parts of acrylic copolymer obtained in the above, 2 parts of dibutyl tin bismonolaurylphthalate and 0.3 part of triphenyl phosphite, and the mixture was dissolved to prepare a spinning solution in concentration of 23 %.

The viscosity of the spinning solution was in the range of 40 to 70 poises at a temperature of 50°C. Then the spinning solution was extruded through the spinneret of nozzle number 300, nozzle diameter 0.1 mm., into the coagulating bath consisting of the same organic solvent as employed in the spinning solution and water, in other words, acetone and water.

The concentration of the coagulating bath was 10, 20, 30 or 40 %, and also the temperature was 10°C., 20°C. or 30°C. The filament formed in the coagulating bath was then introduced into the drawing bath of acetone and water in concentration of 70 %, and was drawn stepwise to 2 or 3 times the original at a temperature of 30°C. Then, the filament was introduced into the washing bath of acetone and water in concentration of 40 % at 30°C. and further introduced into the washing bath of acetone and water in concentration of 5 % at 40°C. in order to remove acetone. The washed filament was introduced into a hot air dryer at a temperature of 115° to 120°C., and thereafter, the filament was heatdrawn 3 times at a temperature of 130°C. Thus obtained drawn fiber of 3 deniers was annealed in a hot air dryer at a temperature of 145°C. for 3 minutes under tension. Thus annealed fiber was employed as a sample fiber for the measurement of fastness to light. Further, the fiber annealed at a temperature of 150°C.

for 10 minutes was employed as a sample fiber for the measurement of heat stability.

The result of fastness to light and heat stability were shown in Table 10.

In table 10, the results in case of the fiber obtained under the condition that the concentration of coagulating bath was 20 %, the temperature of coagulating both was 20°C. and the draw ratio in drawing bath was 3 were shown since these parameters did not influence upon the fastness to light and the heat stability.

5 and the retention ratio to tensile strength was 55.4 % and, therefore, the fiber was also inferior in fastness to light. The copolymer obtained in Comparative Example 18 contained 5.7 % of sodium sulfopropyl-laurylmaleate, and the heat stability and the fastness to light of the modacrylic fiber prepared therefrom were superior, but in case of dyeing the fiber with cationic dyestuff, uneven dyeing occured due to the strong affinity to dyestuffs of the fiber. Also, the copolymer had the disadvantage that it was hardly controlled to remove Table 10

| | Composition for polymerization | | | | | | | | | | |
|---|---|---|---|---|---|---|---|---|---|---|---|
| | Initial charging | | | | | | Continuous charging | | | | |
| Example No. | Acrylo-nitrile | Vinyl chloride | Sodium sulfo-propyl-lauryl-maleate | Sodium meth-allyl sulfo-nate | Sodium mono-lauryl itaco-noxy propane sulfo-nate | Sodium sulfo-propyl meth-acry-late | Sodium dodecyl-benzene sulfo-nate | Acrylo-nitrile | Sodium sulfo-propyl-lauryl-maleate | Sodium mono-lauryl itaco-noxy propane sulfo-nate | Sodium sulfo-propyl meth-acry-late | Yield of polymer |
| | | | | | | part | | | | | | part |
| 27 | 17.5 | 82.5 | 0.3 | — | — | — | 1.5 | 45.6 | 0.5 | — | — | 98.3 |
| 28 | 17.5 | 82.5 | 0.3 | — | — | — | 1.5 | 45.6 | 1.0 | — | — | 97.8 |
| 29 | 17.5 | 82.5 | 0.5 | — | — | — | — | 45.6 | 1.5 | — | — | 101.3 |
| 30 | 17.5 | 82.5 | 0.5 | — | — | — | — | 45.6 | 2.5 | — | — | 100.2 |
| 31 | 17.5 | 82.5 | 0.7 | — | — | — | — | 45.6 | 3.3 | — | — | 99.6 |
| Com. Ex. 17 | 17.5 | 82.5 | 0.3 | — | — | — | 2.0 | 45.6 | — | — | — | 101.2 |
| 18 | 17.5 | 82.5 | 1.0 | — | — | — | — | 45.6 | 5.0 | — | — | 99.2 |
| 19 | 17.5 | 82.5 | — | 3.0 | — | — | 3.0 | 45.6 | — | — | — | 97.8 |
| 20 | 17.5 | 82.5 | — | — | 0.5 | — | — | 45.6 | — | 2.5 | — | 101.4 |
| 21 | 17.5 | 82.5 | — | — | — | 0.5 | 3.0 | 45.6 | — | — | 2.5 | 102.3 |

| | | | | Properties of modacrylic fiber | | | | | | |
|---|---|---|---|---|---|---|---|---|---|---|
| Polymer composition | | | | Heat stability | | | Fastness to light | | | |
| Acrylo-nitrile | Vinyl chloride | Sodium sulfo-propyl-lauryl-maleate | Other poly-merizable material | Whiteness of drawn fiber (a) | Whiteness of annealed fiber (b) | Difference of whiteness (b−a) | Fastness to light | Tensile strength before exposure (G) | Tensile strength after exposure (G') | Retention to tensile strength (G'/G × 100) |
| % | | | | — | | | Class | g./d. | g./d. | % |
| 54.2 | 45.1 | 0.7 | — | 0.160 | 0.170 | 0.010 | 7 | 2.87 | 2.26 | 78.7 |
| 54.0 | 44.9 | 1.1 | — | 0.150 | 0.163 | 0.013 | 7 | 3.02 | 2.61 | 86.4 |
| 53.4 | 44.6 | 2.0 | — | 0.151 | 0.160 | 0.010 | 7 | 2.96 | 2.47 | 83.4 |
| 54.2 | 42.9 | 2.9 | — | 0.150 | 0.160 | 0.010 | 8 | 2.84 | 2.40 | 84.5 |
| 52.4 | 43.8 | 3.8 | — | 0.148 | 0.157 | 0.009 | 8 | 3.06 | 2.51 | 82.1 |
| 55.9 | 43.9 | 0.2 | — | 0.161 | 0.198 | 0.037 | 5 | 3.01 | 1.67 | 55.4 |
| 52.8 | 41.5 | 5.7 | — | 0.147 | 0.158 | 0.011 | 7 | 3.12 | 2.63 | 84.6 |
| 55.0 | 43.6 | — | 1.4 | 0.156 | 0.202 | 0.046 | 4 | 2.96 | 1.41 | 47.6 |
| 54.4 | 42.8 | — | 2.8 | 0.166 | 0.223 | 0.057 | 4 | 2.76 | 1.12 | 40.6 |
| 54.0 | 43.0 | — | 3.0 | 0.169 | 0.220 | 0.051 | 4 | 2.94 | 1.41 | 47.9 |

The copolymers obtained in Examples 27 to 31 contained 0.7 to 3.8 % of sodium sulfopropyl-laurylmaleate being the polymerizable emulsifying agent of the present invention. The heat stability of the modacrylic fibers obtained therefrom was very excellent. It is clear from the result that the difference of whiteness between the annealed fiber and the drawn fiber is about 0.01. It may be said in this connection that the difference of whiteness of more than about 0.02 can be distinguished by the naked eye. The result of fading was Class 7 in each Example and also the retention ratio to tensile strength was more than about 80 % and, therefore, the fastness to light was very excellent.

On the contrary, the copolymer obtained in Comparative Example 17 contained 0.2 % of sodium sulfopropyl-laurylmaleate, and the difference of whiteness between the annealed fiber and the drawn fiber were large and, therefore, the modacrylic fiber was inferior in heat stability. Further, the result of fading was Class the solvent in the coagulating bath and the transparent drawn fiber was hardly obtained, since the hydrophilic property of the copolymer was too strong. Each copolymer obtained in Comparative Examples 19 to 21 included a conventional polymerizable emulsifying agent or sulfonic monomer which were able to act as a modifier for dyeing ability. However, the difference of whiteness of the fiber prepared therefrom was about 0.05 in each case, that is, the heat stability of the fiber was very inferior. It may be said in this connection that a fair coloring can be observed by the naked eye in case the difcrence of whiteness is 0.04 to 0.05. Also the fastness to light of each fiber was Class 4, and the retention ratio to tensile strength was about 40 to 50 %, which was considerably bad.

EXAMPLES 32 TO 36 AND COMPARATIVE EXAMPLES 22 TO 25

Improved modacrylic fiber

[Preparation of acrylic copolymer]

The polymerizations were carried out by employing compositions for initial charging and compositions for continuous charging shown in Table 11 for about 3 to 10 hours by the same manner as in Example 27. The polymerization was carried out for about 3 hours in case of Example 36, and was carried out for about 10 hours in case of Example 32. The composition for continuous charging was continuously introduced into the polymerization system during the polymerization to prepare a copolymer having a uniform composition.

[Preparation of modacrylic fiber]

To acetone or dimethylformamide in an amount shown in Table 11 were added 100 parts of acrylic copolymer obtained in the above polymerization, 1.5 parts of dioctyl tin butoxymonobutylphthalate and 0.6 part of barium tertbutylphenolate, and the mixture was dissolved to prepare a spinning solution in concentration shown in Table 11.

The viscosity of thus obtained spinning solution was in the range of 30 to 90 poises. The drawn fiber and the annealed fiber were prepared by the same manner as in Example 27 except that the coagulating bath consisted of acetone or dimethylformamide and water in accordance with the solvent employed in the preparation of the spinning solution.

The results of heat stability and fastness to light were shown in Table 11.

fiber and the drawn fiber of the modacrylic fiber prepared therefrom were in the range of 0.015 to 0.008 and, therefore, the heat stability of the fiber was very excellent. Also, the fastness to light was superior to Class 6 in each case. In the case where the content of acrylonitrile was not less then 44.6 %, the fastness to light was superior to Class 7 and, therefore, the fastness to light was very excellent. The fastness to light of the fiber in Example 32 was Class 6. However, it is clear that the fastness to light of the fiber is well improved in comparison with the fastness of the fiber in Comparative Example 22 being Class 3. Further, the retention to tensile strength of the fibers after fading was more than about 80 %. It is clear that the fibers are well improved in comparison with the fibers in Comparative Examples 22 and 23.

In Comparative Example 22, the heat stability and the fastness to light of the fiber were not improved despite that the copolymer contained 2.9 % of sodium sulfopropyl-laurylmaleate, because the content of acrylonitrile was 24.1 %. Comparative Example 23 shows the case that the present polymerizable emulsifying agent is not contained, and the fiber is inferior in heat stability and fastness to light in spite of large quantities of acrylonitrile content which is 65.5 %. In general, the heat stability and the fastness to light of the modacrylic fiber depend on the acrylonitrile content of the copolymer, and the more the acrylonitrile content, the better Table 11

| | Composition for polymerization | | | | | | | Polymer composition | | | |
|---|---|---|---|---|---|---|---|---|---|---|---|
| | Initial charging | | | | Continuous charging | | | | | | |
| Example No. | Acrylo-nitrile | Vinyl chloride | Sodium sulfo-propyl-lauryl-maleate | Sodium methallyl sulfonate | Sodium dodecyl-benzene sulfo-nate | Acrylo-nitrile | Sodium sulfo-propyl-lauryl-maleate | Yield of polymer | Acrylo-nitrile | Vinyl chloride | Sodium sulfo-propyl-lauryl-maleate | Other poly-meri-zable mate-rial |
| | part | | | | | part | | | % | | | |
| 32 | 6.3 | 93.7 | 0.5 | — | 0.3 | 31.7 | 2.5 | 98.7 | 35.1 | 62.1 | 2.8 | — |
| 33 | 11.2 | 88.8 | 0.5 | — | 0.3 | 39.3 | 2.5 | 100.3 | 44.6 | 52.5 | 2.9 | — |
| 34 | 17.5 | 82.5 | 0.6 | — | 0.3 | 45.6 | 2.5 | 101.0 | 54.4 | 42.7 | 2.9 | — |
| 35 | 28.1 | 71.9 | 0.6 | — | 0.5 | 52.1 | 2.6 | 98.4 | 64.4 | 32.6 | 3.0 | — |
| 36 | 35.2 | 64.8 | 0.7 | — | 0.7 | 55.2 | 2.6 | 102.1 | 69.5 | 27.3 | 3.2 | — |
| Com. Ex. 22 | 3.2 | 96.8 | 0.5 | — | 0.3 | 22.3 | 2.5 | 99.2 | 24.1 | 73.0 | 2.9 | — |
| 23 | 28.1 | 71.9 | — | 2.5 | 3.5 | 52.1 | — | 102.4 | 65.5 | 33.6 | — | 0.9 |
| 24 | 60.2 | 39.8 | 0.8 | — | 0.7 | 63.0 | 2.5 | 99.3 | 83.5 | 13.3 | 3.2 | — |
| 25 | 60.2 | 39.8 | — | 2.5 | 4.0 | 63.0 | — | 98.9 | 84.9 | 14.3 | — | 0.8 |

| | Spinning solution | | Properties of modacrylic fiber | | | | | | |
|---|---|---|---|---|---|---|---|---|---|
| | | | Heat stability | | | | Fastness to light | | |
| Organic solvent | Amount of organic solvent | Concent-ration of spinning solution | Whiteness of drawn fiber (a) | Whiteness of annealed fiber (b) | Difference of white-ness (b–a) | Fastness to light | Tensile stren-gth before expo-sure (G) | Tensile stren-gth after expo-sure (G') | Retention to tensile strength (G'/G × 100) |
| — | part | % | | | | Class | g./d. | g./d. | % |
| acetone | 290 | 26.2 | 0.177 | 0.192 | 0.015 | 6 | 2.73 | 2.09 | 76.5 |
| acetone | 320 | 24.3 | 0.160 | 0.172 | 0.012 | 7 | 2.82 | 2.39 | 84.7 |
| acetone | 360 | 22.2 | 0.152 | 0.161 | 0.009 | 7 | 3.04 | 2.65 | 87.2 |
| dimethylformamide | 400 | 20.4 | 0.144 | 0.152 | 0.008 | 8 | 3.27 | 2.91 | 89.0 |
| dimethylformamide | 410 | 20.0 | 0.147 | 0.158 | 0.011 | 8 | 3.62 | 3.28 | 90.5 |
| acetone | 280 | 26.9 | 0.203 | 0.252 | 0.049 | 3 | 2.54 | 1.09 | 42.9 |
| dimethylformamide | 410 | 20.0 | 0.151 | 0.193 | 0.042 | 5 | 3.31 | 2.16 | 65.3 |
| dimethylformamide | 455 | 18.1 | 0.130 | 0.143 | 0.013 | 8 | 3.71 | 3.43 | 92.4 |
| dimethylformamide | 455 | 18.1 | 0.131 | 0.146 | 0.015 | 8 | 3.56 | 3.16 | 88.7 |

The copolymers obtained in Examples 32 to 36 contained 2.8 to 3.2 % of sodium sulfopropyl-laurylmaleate being the polymerizable emulsifying agent of the present invention, and 35.1 to 69.5 % of acrylonitrile. The differences of whiteness between the annealed both properties tend to become. Therefore, the comparison should be done between fibers having the similar acrylonitrile content to each other. Comparative Examples 24 and 25 show the cases in which the present polymerizable emulsifying agent is contained and is not contained, respectively. However, the acrylonitrile content in each case is about 84 %, and the heat stability and the fastness to light are excellent. It has been known that such an acrylic fiber is superior in heat stability and fastness to light, and there is no room for improvement.

EXAMPLES 37 TO 41 AND COMPARATIVE EXAMPLES 26 TO 30

Improved modacrylic fiber in Example 27 except that the coagulating bath was 40, 50 or 60 % aqueous solution of dimethylformamide and the drawing bath was 60 % aqueous solution of dimethylformamide.

The result of heat stability and fastness to light were shown in Table 12.

In Table 12, the results in case of the fiber obtained under the condition that the concentration of coagulating bath 50 % were shown by the same reason mentioned in Example 27.

Table 12

| | Composition for polymerization ||||||||||
|---|---|---|---|---|---|---|---|---|---|
| | Initial charging ||||| | Continuous charging ||||
| Example No. | Acrylo-nitrile | Vinylidene chloride | Sodium sulfo-propyl-cetyl-maleate | Sodium methallyl sulfonate | Sodium mono-lauryl itaco-noxy propane sulfo-nate | Sodium lauryl sulfate | Acrylo nitrile | Sodium sulfo-propyl-cetyl-maleate | Sodium mono-lauryl itaco-noxy propane sulfonate |
| | part ||||| | part |||
| 37 | 25.9 | 74.1 | 2.1 | — | — | 0.3 | 12.7 | 0.9 | — |
| 38 | 37.3 | 62.7 | 2.3 | — | — | 0.3 | 13.3 | 0.7 | — |
| 39 | 51.5 | 48.5 | 2.5 | — | — | 0.3 | 9.3 | 0.5 | — |
| 40 | 67.0 | 33.0 | 3.0 | — | — | 0.5 | 4.9 | — | — |
| 41 | 72.1 | 27.9 | 3.0 | — | — | 0.5 | 2.5 | — | — |
| Com. | | | | | | | | | |
| Ex. 26 | 15.3 | 84.7 | 1.7 | — | — | — | 11.6 | 1.3 | — |
| 27 | 51.5 | 48.5 | — | 3.0 | — | 0.3 | 9.3 | — | — |
| 28 | 51.5 | 48.5 | — | — | 2.5 | 0.3 | 9.3 | — | 0.5 |
| 29 | 83.1 | 16.9 | 3.0 | — | — | 0.5 | — | — | — |
| 30 | 83.1 | 16.9 | — | 3.0 | — | 3.0 | — | — | — |

| | Polymer composition |||| Spinning solution || Properties of modacrylic fiber |||||
|---|---|---|---|---|---|---|---|---|---|---|---|
| | | | | | | | Heat stability ||| Fastness to light |||
| Yield of polymer | Acrylo-nitrile | Vinylidene chloride | Sodium sulfo-propyl cetyl-maleate | Other poly-meri-zable mate-rial | Amount of di-methyl-form-amide | Concent-ration of spinning solution | White-ness of drawn fiber (a) | White-ness of anneal-ed fiber (b) | Differ-rence of white-ness (b–a) | Fast-ness to light | Tensile stren-gth before expo-sure (G) | Tensile stren-gth after expo-sure (G') | Retention to tensile strength (G'/G × 100) |
| part | % |||| part | % | | | | Class | g./d. | g./d. | % |
| 102.3 | 34.0 | 63.1 | 2.9 | — | 295 | 25.9 | 0.172 | 0.189 | 0.017 | 6 | 2.97 | 2.37 | 79.8 |
| 101.9 | 43.7 | 53.4 | 2.9 | — | 335 | 23.5 | 0.157 | 0.172 | 0.015 | 6 | 3.06 | 2.56 | 83.6 |
| 101.8 | 54.8 | 42.4 | 2.8 | — | 365 | 22.0 | 0.149 | 0.162 | 0.013 | 7 | 3.41 | 2.92 | 85.6 |
| 97.0 | 66.5 | 31.5 | 3.0 | — | 385 | 21.1 | 0.137 | 0.152 | 0.015 | 7 | 3.48 | 3.05 | 87.6 |
| 95.8 | 70.8 | 26.3 | 2.9 | — | 400 | 20.5 | 0.134 | 0.150 | 0.016 | 8 | 3.54 | 3.27 | 92.3 |
| 99.3 | 24.4 | 72.7 | 2.9 | — | 280 | 26.9 | 0.197 | 0.251 | 0.054 | 2 | 2.66 | 1.11 | 41.7 |
| 98.2 | 55.3 | 43.5 | — | 1.2 | 365 | 22.0 | 0.152 | 0.194 | 0.042 | 5 | 3.48 | 1.99 | 57.2 |
| 96.5 | 54.5 | 42.7 | — | 2.8 | 365 | 22.0 | 0.155 | 0.204 | 0.049 | 4 | 3.37 | 1.78 | 52.8 |
| 96.7 | 81.5 | 15.6 | 2.9 | — | 410 | 20.1 | 0.128 | 0.141 | 0.013 | 8 | 3.77 | 3.46 | 91.7 |
| 95.2 | 82.1 | 16.6 | — | 1.3 | 410 | 20.1 | 0.131 | 0.147 | 0.016 | 8 | 3.69 | 3.31 | 89.7 |

[Preparation of acrylic copolymer]

The polymerizations were carried out by employing compositions for initial charging and compositions for continuous charging shown in Table 12 by the same manner as in Example 27. The composition for continuous charging was continuously introduced into the polymerization system during the polymerization to prepare a copolymer having a uniform composition.

[Preparation of modacrylic fiber]

To dimethylformamide in an amount shown in Table 12 were added 100 parts of acrylic copolymer obtained in the above polymerization, 1.5 parts of dibutyl tin benzoate, 0.5 part of dibutyl tin mercaptide and 0.5 part of triphenyl phosphite, and the mixture was dissolved to prepare a spinning solution in concentration shown in Table 12. The viscosity of thus obtained spinning solution was in the range of 30 to 110 poises at a temperature of 50°C. The drawn fiber and the annealed fiber of 3 deniers were prepared by the same manner as The copolymers obtained in Examples 37 to 41 contained 2.8 to 3.2 % of sodium sulfopropyl-cetylmaleate being the polymerizable emulsifying agent of the present invention, and 34.0 to 70.8 % of acrylonitrile. The differences of whiteness between the annealed fiber and the drawn fiber of the modacrylic fiber prepared therefrom were in the range of 0.017 to 0.013 and, therefore, the heat stability of the fiber was very excellent compared with the differences of whiteness in Comparative Examples 26 to 28 were in the range of 0.042 to 0.054. Also, the fastness to light was over Class 6 in each Example and was excellent. For instance, in case of comparing the fiber in Example 39 with the fibers in Comparative Example 27 and 28 of which acrylonitrile content is similar to the fiber in Example 39, it is clear that the polymerizable anionic emulsifying agent of the invention more contributes to improve the heat stability and the fastness to light of the fiber than the conventional emulsifying agents employed in Comparative Examples 27 and 28. Further, the retention to tensile strength of the fibers after fading was more than about 80 %. It is clear that the fastness to light of the fibers is well improved in comparison with that of the fibers in Comparative Examples 26 to 28.

In Comparative Example 26, the heat stability and the fastness to light of the fiber were not improved despite that the copolymer contained 2.9 % of sodium sulfopropyl-cetylmaleate, since the content of acrylonitrile was 24.4 %. Comparative Examples 29 and 30 show the cases that the present polymerizable emulsifying agent is contained and is not contained, respectively. However, the acrylonitrile content in each case is about 82 %, and the heat stability and the fastness to light are excellent. It has been known that such an acrylic fiber is superior in heat stability and fastness to light, and there is no room for improvement.

What we claim is:

1. In a process for polymerizing an α,β-ethylenically-unsaturated monomer and a polymerizable emulsifying agent by aqueous emulsion polymerization in the presence of a water-soluble polymerization initiator, the improvement which comprises polymerizing 93 to 99.5 % by weight of α,β-ethylenically unsaturated monomer having a solubility in water of not more than 10 % by weight at 35°C., 0 to 2 % by weight of α,β-ethylenically unsaturated monomer having a solubility in water of more than 10 % by weight at 35°C. and 0.5 to 5 % by weight of polymerizable anionic emulsifying agent having the following general formula:

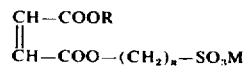

wherein R is an alkyl group having 6 to 22 carbon atoms, M is H, Li, Na, K or NH$_4$ and n is an integer of 2 to 4, inclusive.

2. The process of claim 1, wherein 2 to 4 % by weight of said polymerizable emulsifying agent is employed.

3. The process of claim 1, wherein said polymerizable anionic emulsifying agent is sodium sulfopropyl-laurylmaleate, sodium sulfopropyl-cetylmaleate, sodium sulfopropyl-2-ethylhexylmaleate or sodium sulfopropyl-tridecylmaleate.

4. The process of claim 1, wherein said α,β-ethylenically unsaturated monomers having a solubility in water of not more than 10 % by weight at 35°C. are a mixture of acrylonitrile and vinyl chloride.

5. The process of claim 1, wherein said α,β-ethylenicallly unsaturated monomers having a solubility in water of not more than 10 % by weight at 35°C. are a mixture of acrylonitrile and vinylidene chloride.

6. The process of claim 1, wherein said α,β-ethylenically unsaturated monomer having a solubility in water of more than 10 % by weight at 35°C. is at least one selected from the group consisting of acrylamide, N-vinylpyrrolidone, acrylic acid, methacrylic acid, allyl sulfonic acid, methacrylic sulfonic acid, p-styrene sulfonic acid, and alkali salts thereof.

7. A modacrylic fiber consisting essentially of a copolymer prepared by polymerizing 30 to 80 % by weight of acrylonitrile, 69.5 to 19.5 % by weight of vinyl chloride or vinylidene chloride and 0.5 to 5 % by weight of a compound having the following general formula:

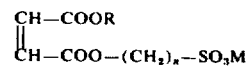

wherein R is alkyl group having 6 to 22 carbon atoms, M is H, Li, Na, K or NH$_4$ and n is an integer of 2 to 4, inclusive.

8. The modacrylic fiber of claim 7, wherein 35 to 75 % by weight of said acrylonitrile and 64.5 to 29.5 % by weight of said vinyl chloride or said vinylidene chloride are employed.

9. The modacrylic fiber of claim 7, wherein not more than 3 % by weight of said α,β-ethylenically unsaturated monomer having a solubility of more than 10 % by weight to water at 35°C. is further copolymerized.

* * * * *